United States Patent [19]

Demerson et al.

[11] 4,012,511
[45] Mar. 15, 1977

[54] OXAZINOINDOLE DERIVATIVES USEFUL AS ANTIDEPRESSANTS

[75] Inventors: Christopher A. Demerson, Montreal; Leslie G. Humber, Dollard des Ormeaux; George Santroch, Montreal; Thomas A. Dobson, Dollard des Ormeaux; Ivo Jirkovsky, Montreal, all of Canada

[73] Assignee: Ayerst McKenna & Harrison Ltd., Montreal, Canada

[22] Filed: July 7, 1975

[21] Appl. No.: 593,582

Related U.S. Application Data

[63] Continuation-in-part of Ser. No. 473,646, May 28, 1974, Pat. No. 3,962,236, and Ser. No. 226,287, Feb. 14, 1972, Pat. No. 3,833,575.

[52] U.S. Cl. .................. 424/248.4; 260/244 R; 260/246 B; 424/248.55; 424/248.57; 424/248.58
[51] Int. Cl.² ............... A01N 9/00; A01N 9/22; C07D 265/00; C07D 273/00
[58] Field of Search ........... 260/244, 246; 424/248

[56] References Cited

UNITED STATES PATENTS

| | | | |
|---|---|---|---|
| 3,532,719 | 10/1970 | Theimer | 260/345.2 |
| 3,676,439 | 7/1972 | Hoffer | 260/243 R |
| 3,833,575 | 9/1974 | Demerson et al. | 260/244 |
| 3,852,284 | 12/1974 | Fauran | 424/248 |

FOREIGN PATENTS OR APPLICATIONS 2,051,496  4/1971  Germany

OTHER PUBLICATIONS

Rieche et al., "Synthetic Methods of Org. Chem.," vol. 12, p. 361, S. Karger (pub.), N.Y. (1958).
Warren et al., "Synthetic Methods of Org. Chem.," vol. 13, pp. 361–362, S. Karger (pub.), N.Y. (1959).

*Primary Examiner*—Albert T. Meyers
*Assistant Examiner*—D. W. Robinson

[57] ABSTRACT

Oxazinoindole derivatives characterized by having an amino(lower)alkyl radical attached to the 1 position of a 1H-1,4-oxazino[4,3-a]indole nucleus are disclosed. The amino portion of the amino(lower)alkyl radical may be further substituted with one or two lower alkyl groups or incorporated in a heterocyclic amine radical. The derivatives are substituted further at positions 1 and 10 and may be optionally substituted at positions 3, 4, 6, 7, 8 and 9. The oxazinoindole derivatives of this invention are useful antidepressant and antiulcer agents. Methods for the use of these derivatives and compositions containing them are also disclosed.

31 Claims, No Drawings

OXAZINOINDOLE DERIVATIVES USEFUL AS ANTIDEPRESSANTS

This Application is a Continuation-in-Part of each of our earilier filed U.S. applications Ser. No. 473,646, filed May 28, 1974, now U.S. Pat. No. 3,962,236, issued June 8, 1976, and Ser. No. 226,287, filed Feb. 14, 1972, now U.S. Pat. No. 3,833,575, issued Sept. 3, 1974.

BACKGROUND OF THE INVENTION

1. Field of Invention

This invention relates to novel oxazinoindole and thiazinoindole derivatives, to processes for their preparation and to intermediates used in these processes. For convenience, further reference in this specification will be made to these compounds as oxazinoindole derivatives.

More specifically, the present invention relates to oxazinoindole derivatives possessing valuable pharmacologic properties. For example, these derivatives exhibit useful antidepressant properties at dosages which do not elicit undesirable side effects. Furthermore the present derivatives exhibit properties useful for the treatment and prevention of ulcers. The combination of these pharmacologic properties together with a low order of toxicity render the oxazinoindoles of the invention therapeutically useful.

2. Description of the Prior Art

Very little attention has been given to 1,4-oxazino[4,3-a]indole derivatives prior to this disclosure. In the few reports that do exist, such as the reports by J. A. Elvridge and F. S. Spring, J. Chem. Soc., 2935 (1949) and W. R. Smith and R. Y. Moir, Can. J. Chem., 30, 411 (1952), the oxazinoindole derivatives are treated more in the reports of chemical curiosities. In these instances, the oxazinoindoles are distinguished readily from the compounds of this invention by having the pyran portion of their ring system at a higher oxidation state.

SUMMARY OF THE INVENTION

The oxazinoindole derivatives of this invention are characterized by having an amino(lower)alkyl radical attached to a 1H-1,4oxazino[4,3-a]indole nucleus. The preferred derivatives of this invention are represented by formula I,

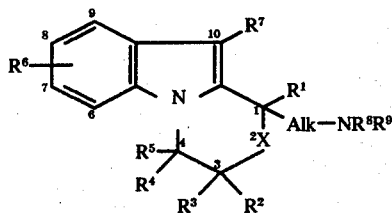

in which $R^1$ is lower alkyl or lower cycloalkyl; $R^2$, $R^3$, $R^4$ and $R^5$ are the same or different selected from the group consisting of hydrogen or lower alkyl; $R^6$ is hydrogen, lower alkyl, hydroxy, lower alkoxy, lower alkanoyloxy, nitro or halo, $R^7$ is lower alkyl; X is oxy or thio; and Alk-$NR^8R^9$ is an amino(lower)alkyl radical in which Alk is an alkylene selected from the group consisting of $CR^{10}R^{11}$, $CR^{10}R^{11}CR^{12}R^{13}$, $CR^{10}R^{11}CR^{12}R^{13}CR^{14}R^{15}$ and $CR^{10}R^{11}CR^{12}R^{13}CR^{14}R^{15}CR^{16}R^{17}$ in which $R^{10}$, $R^{11}$, $R^{12}$, $R^{13}$, $R^{14}$, $R^{15}$, $R^{16}$ and $R^{17}$ are hydrogen or lower alkyl, and $R^8$ and $R^9$ are either the same or different selected from the group consisting of hydrogen and lower alkyl, or $R^8$ and $R^9$ together with the nitrogen atom to which they are joined form a heterocyclic amine radical selected from the group consisting of 1-pyrrolidinyl, piperidino, morpholino, piperazino, 4-(lower alkyl)-1-piperazinyl and 4-[hydroxy(lower)alkyl]-1-piperazinyl.

DETAILED DESCRIPTION OF THE INVENTION

The term "lower alkyl" as used herein contemplates straight chain alkyl radicals containing from one to six carbon atoms and branched chain alkyl radical containing up to four carbon atoms and includes methyl, ethyl, propyl, isopropyl, butyl, isobutyl, 2-methylpentyl and the like.

The term "lower cycloalkyl" as used herein contemplates saturated cyclic hydrocarbon radicals containing from three to six carbon atoms and includes cyclopropyl, cyclobutyl, cyclopentyl and cyclohexyl.

The term "lower alkoxy" as used herein contemplates both straight and branched chain alkoxy radicals containing from one to four carbon atoms and includes methoxy, ethoxy, isopropoxy, t-butoxy and the like.

The term "lower alkanoyloxy" as used herein contemplates both straight and branched chain alkanoyloxy radicals containing from two to six carbon atoms and includes acetoxy, propionyloxy, pivaloyloxy, hexanoyloxy and the like.

The term "halo" as used herein contemplates halogens and includes fluorine, chlorine, bromine and iodine.

The compounds of formula I are capable of forming acid addition salts with pharmaceutically acceptable acids. Such acid addition salts are included within the scope of this invention.

The acid addition salts are prepared by reacting the base form of the appropriate compound of formula I with either one or two equivalents, depending on the number of basic nitrogens in the compound, or preferably with an excess of the appropriate acid in an organic solvent, for example, ether or an ethanol-ether mixture. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

Also included in this invention are the stereochemical isomers of the compounds of formula I which result from asymmetric centers, contained therein. These isomeric forms may be prepared by different methods and are purified readily by crystallizaton or chromatography.

Individual optical isomers, which might be separated by fractional crystallization of the diastereoisomeric salts formed thereof, for instance, with d- or l-tartaric acid or D-(+)-α-bromocamphor sulfonic acid, are also included.

ANTIDEPRESSANT ACTIVITY

The useful antidepressant activity of the compounds of formula I and their acid addition salts with pharmaceutically acceptable acids may be demonstrated in standard pharmacologic tests, such as, for example, the tests described by F. Hafliger and V. Burckhart in "Psychopharmacological Agents", M. Gordon, Ed., Academic Press, New York and London, 1964, pp. 75–83.

More specifically, as noted in the latter reference the antidepressant properties of a compound may be demonstrated by its capacity to antagonize the depressant effects of reserpine. Furthermore, it is well documented that reserpine in animals products a model depression which can be used for detecting antidepressant properties. Accordingly, the compounds of the present invention antagonize reserpine effects in mice at doses ranging from about 1 to 100 mg/kg. Several of the preferred compounds, for instance, 1,10-dimethyl-1-[2-(ethylamino)ethyl]-3,4-dihydro-1H-1,4-oxazino[4,3-a]indole hydrobromide (Example 284), 1,10-dimethyl-1-[(2-dimethylamino)ethyl]-3,4-dihydro-1H-1,4-oxazino[4,3-a]indole hydrochloride (Example 284), 1-(3-aminopropyl)-1,10-dimethyl-3,4-dihydro-1H-1,4-oxazino[4,3-a]indole hydrochloride (Example 286), 1,10-dimethyl-1-[3-(methylamino)propyl]-3,4-dihydro-1H-1,4-oxazino[4,3-a]indole hydrochloride (Example 285) and 1,10-dimethyl-1-[3-(dimethylamino)propyl]-3,4-dihydro-1H-1,4-oxazino[4,3-a]indole hydrochloride (Example 287), antagonize the effects of reserpine in mice at dose ranges from about 1 to 10 mg/kg.

When the compounds of this invention are used as antidepressants in warm-blooded mammals, e.g. rats and mice, they may be used alone or in combination with pharmacologically acceptable carriers, the proportion of which is determined by the solubility and chemical nature of the compound, chosen route of administration and standard biological practice. For example, they may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side efects and preferably at a level that is in a range of from about 0.1 mg to about 50 mg per kilo per day, although as aforementioned variations will occur. However, a dosage level that is in the range of from about 0.5 mg to about 25 mg per kilo per day is most desirably employed in order to achieve effective results.

ANTIULCER ACTICITY

The compounds of formula I of this invention possess another useful pharmacologic property; that is, they are useful antiulcer agents. More particularly, the said compounds of this invention exhibit antiulcer activity in standard pharmacologic tests, for example, the test described by D. A. Brodie and L. S. Valitski, Proc. Soc. Exptl. Biol. Med., 113, 998 (1963), based on the prevention of stress-induced ulcers.

When the compounds of formula I are employed as antiulcer agents, they may be formulated and administered in the same manner as described above for their use as antidepressant agents.

PROCESSES

For the preparation of the oxazinoindoles of this invention we prefer to use as starting materials the compounds of formula II,

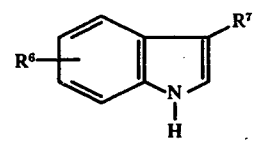

in which $R^6$ and $R^7$ are as defined in the first instance.

The starting materials of formula II are either well known, for example, skatole and 3-ethylindole, or they may be prepared from indole or known indole derivatives, for example, see P. L. Julian, et al., "Heterocyclic Compounds", R. C. Elderfield, Ed., Vol. 3, John Wiley and Sons, Inc., New York, 1952, p. 1, according to the method of R. Robinson, et al., described in U.S. Pat. No. 2,407,452, issued Sept. 10, 1946.

The starting material of formula II is then converted to the key intermediate of formula III,

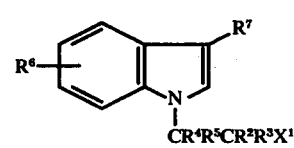

in which $R^2$, $R^3$, $R^4$, $R^5$, $R^6$ and $R^7$ are as defined in the first instance and $X^1$ is hydroxy or mercapto.

This conversion may be effected by several methods. One general method involves reacting the appropriate lithium derivative of the starting material of formula II with ethylene oxide or an appropriate lower alkyl substituted ethylene oxide to afford the desired intermediate of formula III in which $X^1$ is hydroxy. The desired intermediates may also be obtained by treating the appropriate starting material of formula II with the appropriate ethylene oxide derivative according to the procedure of M. Julia, et al., Bull. Soc. Chim. Fr., 2291 (1966).

The lower alkyl substituted ethylene oxides are prepared by known methods; for example, see V. Franzen and H. E. Driesen, Chem. Ber., 96, 1881 (1963).

An alternative method for the preparation of intermediates of formula III in which $R^2$ and $R^3$ are hydrogen involves treating the starting material of formula II with an α-haloacetic acid lower alkyl ester of formula $LCR^4R^5COO$(lower alkyl) in which L is halo and $R^4$ and $R^5$ are as defined in the first instance, in the presence of a suitable proton acceptor and using preferably an inert solvent for the reaction. The α-haloacetic acid lower alkyl esters are well known, for example see "Rodd's Chemistry of the Carbon Compounds", S. Coffey, Ed., Vol. Ic, 2nd ed., Elsevier Publishing Co., Amsterdam, 1965, pp. 201–205. Suitable proton acceptors include sodium hydride, alkali metal carbonates and triethylamine. Suitable inert solvents include tetrahydrofuran, benzene, toluene and dimethylformamide. Preferred conditions for the N-alkylation include the use of sodium hydride as a proton acceptor and tetrahydrofuran as an inert solvent. Although the optimum temperature and reaction time will vary depending on the reactants employed, the reaction is generally performed at the boiling point of the reaction mixture for a period of 30 minutes to 48 hours.

The indole-1-acetic acid lower alkyl ester derivative obtained by the above N-alkylation reaction is thereafter hydrolyzed, preferably with a solution of potassium hydroxide in methanol water, to give the corresponding indole-1-acetic acid derivatives which on reduction with lithium aluminum hydride affords the desired intermediate of formula III in which $R^2$ and $R^3$ are hydrogen and $X^1$ is hydroxy.

Again alternatively, the latter indole-1-acetic acid derivative may also be reacted with two equivalents of a lower alkyl Grignard reagent, for example, methyl magnesium bromide, to give, after hydrolysis of the magnesium-halogen derivative, the desired intermediates of formula III ($R^2=R^3=$ lower alkyl and $X^1 =$ hydroxy), see L. F. Fieser and M. Fieser, "Advanced Organic Chemistry", Reinhold Publishing Corp., New York, 1961, p. 272.

When the corresponding intermediates of formula III in which $X^1$ is mercapto are desired a procedure similar to that described by N. N. Suvorov and V. N. Buyanov, Khim.-Farm. ZH., 1, (1967), [Chem. Abstr. 67. 73474a (1967)], for converting 3-(2-bromoethyl)-indole to indole-3-ethanethiol, may be employed. More particularly, the above intermediate of formula III in which $X^1$ is hydroxy is treated with phosphorus tribromide in an inert solvent, for example, ether or carbon tetrachloride, followed by treatment of the product with sodium or potassium thiosulfate to afford the corresponding sodium or potassium β-(1indolyl)ethyl thiosulfate derivative, respectively. Treatment of the latter product with strong alkali, for example, sodium or potassium hydroxide, yields the corresponding bis-[ω-(indolyl)ethyl]disulfide derivative. Finally reduction of the latter compound with lithium aluminum hydride gives the desired intermediate of formula III in which $X^1$ is mercapto.

Alternatively, the starting materials of formula III in which $R^2$ and $R^3$ are hydrogen and $X^1$ is mercapto may be prepared by oxidizing the corresponding intermediate of formula III in which $X^1$ is hydroxy, described above, with N,N-dicyclohexylcarbodiimide and dimethyl sulfoxide in the presence of a suitable acid, for example, trifluoroacetic acid, see K. E. Pfitzner and J. G. Moffat, J. Amer. Chem. Soc., 87, 5670 (1965), to give the corresponding aldehyde derivative. The same aldehyde derivative may also be obtained by N-alkylation of the appropriate starting material of formula II with an appropriate α-halo-acetaldehyde derivative (see "Rodd's Chemistry of the Carbon Compounds", Vol., 1c, pp. 24–26) according to the cited above, conditions described above for N-alkylation with α-haloacetic acid lower alkyl esters.

The latter aldehyde derivative is converted to its corresponding gem-dithiol derivative with hydrogen sulfide, which is reduced with lithium aluminum hydride, according to the method of T. L. Cairns, et. al., J. Amer. Chem. Soc., 74, 3982 (1952), to yield the desired starting material of formula III.

It should be noted that the preceding processes may not be entirely practical for the preparation of the compounds of formula III in which $X^1$ is hydroxy or mercapto and $R^6$ is hydroxy or lower alkanoyloxy. For this reason, the preferred starting materials of formula II for the ultimate preparation of the compounds of formula I in which $R^6$ is hydroxy or lower alkanoyloxy are the corresponding compounds of formula II in which $R^6$ is benzyloxy, i.e. a hydroxyl with a protecting benzyl group or other suitable protecting group (see J. F. W. McOmie, "Advances in Organic Chemistry", Vol. 3, R. A. Raphael, et al., Ed., Interscience Publishers, New York, 1963, pp. 191–294). After the appropriate transformations described below, the benzyloxy group is removed by hydrogenation, in the presence of a catalyst, for example, 10% palladium on carbon, just prior to affording the desired corresponding compound of formula I in which $R^6$ is hydroxy. The latter may be converted if desired to the corresponding compound of formula I in which $R^6$ is lower alkanoyloxy by conventional means, for example, by treatment with the appropriate lower alkanoic anhydride preferably in the presence of pyridine.

The above described intermediate of formula III in which $R^2$, $R^3$, $R^4$, $R^5$, $R^6$, $R^7$ and $X^1$ are as defined in the first instance are now subjected to a key reaction comprising the treatment of said starting materials with a compound of formula

(IV)

in which $R^1$ is as defined in the first instance and Z is selected from the group consisting of:
a. $COOR^{18}$ and $Alk^1 — COOR^{18}$ in which $R^{18}$ is hydrogen or lower alkyl and $Alk^1$ is an alkylene selected from the group consisting of $CR^{10}R^{11}$, $CR^{10}R^{11}CR^{12}R^{13}$ and $CR^{10}R^{11}CR^{12}R^{13}CR^{14}R^{15}$ wherein $R^{10}$, $R^{11}$, $R^{12}$, $R^{13}$, $R^{14}$ and $R^{15}$ are hydrogen or lower alkyl,
b. $CONR^8R^9$ and $Alk^1—CONR^8R^9$ in which $Alk^1$, $R^8$ and $R^9$ are as defined above,
c. $CH_2OCOR^{19}$ and $Alk^1—CH_2OCOR^{19}$ in which $R^{19}$ is hydrogen or lower alkyl and $Alk^1$ is as defined above,
d. $Alk^2—L$ in which $Alk^2$ is an alkylene selected from the group consisting of $CR^{10}R^{11}CHR^{12}$, $CR^{10}R^{11}CR^{12}R^{13}CHR^{14}$ and $CR^{10}R^{11}CR^{12}R^{13}CR^{14}R^{15}CHR^{16}$ wherein $R^{10}$, $R^{11}$, $R^{12}$, $R^{13}$, $R^{14}$, $R^{15}$ and $R^{16}$ are as defined above and L is halo,
e. $Alk\ NR^8COR^{20}$ in which Alk and $R^8$ are as defined in the first instance and $R^{20}$ is hydrogen or lower alkyl containing from one to five carbon atoms, and
f. $Alk—NO_2$ in which Alk is as defined in the first instance, in the presence of an acid catalyst to yield the compounds of formula V in which $R^1$, $R^2$, $R^3$, $R^4$, $R^5$, $R^6$, $R^7$, X and Z are as defined above.

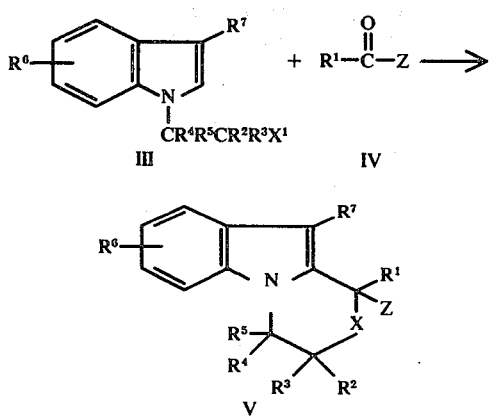

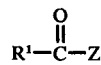

in which $R^1$ is as defined in the first instance and Z is $COOR^{18}$ or $Alk^1$—$COOR^{18}$ as defined above together with the intermediate of formula III.

Generally comparable yields of product are obtained in this process when either the ketoacid or the corresponding ketoester is used. However, in the case where it is desired to prepare an acid compound of formula V in which Z is $Alk^1COOR^{18}$ wherein $Alk^1$ is $CR^{10}R^{11}$ and $R^{18}$ is hydrogen (i.e., an acid intermediate of formula V), it is preferable to first condense the appropriate β-ketoester of formula IV rather than the corresponding β-ketoacid and they hydrolyze the resulting ester product to give the desired acid compound.

Moreover, in the general practice of this invention it is often more convenient to prepare the acid compounds of formula V by using the ketoester instead of the ketoacid in this process and then hydrolyze the resulting ester product to the desired acid, the reason being simply that the ketoesters are generally more readily available either commercially or by synthesis.

Compounds of formula V in which Z is $COOR^{18}$ or $Alk^1COOR^{18}$ wherein $Alk^1$ is as defined in the first instance and $R^{18}$ is lower alkyl, i.e. ester intermediates of formula V, are hydrolyzed readily to their corresponding acids of formula V by treatment with a suitable alkali, for example, potassium hydroxide or sodium carbonate, in aqueous methanol or aqueous ethanol or by treatment with lithium iodide in a suitable organic solvent, for example, collidine, see L. F. Fieser and M. Fieser, "Reagents for Organic Synthesis", John Wiley and Sons, Inc., New York, 1967, pp. 615–617.

The α-, β-, γ-, and δ-ketoacids and -ketoesters of formula III are either known, for example, ethyl pyruvate, levulinic acid, ethyl α,α-dimethylacetoacetate and β,β-dimethyllevulic acid or they may be prepared by known methods decribed in general organic chemistry textbooks. For example, a comprehensive review on the properties and preparation of such α-, β-, γ-, and δ-ketoacids and -ketoesters may be found in "Rodd's Chemistry of the Carbon Compounds", cited above, Vol. Id, pp. 226–274.

Thereafter the appropriate compound of formula V is converted to the desired oxazinoindole of formula I according to the processes described hereinafter.

In practising the condensation (III + VI →V) we have found it preferable to use a solvent as a reaction medium. Any solvent inert to the reaction conditions may be used. Suitable solvents include aromatic hydrocarbons, for example, benzene or toluene, ethers and cyclic ethers, for example, diethyl ether, dioxan or tetrahydrofuran, halogenated hydrocarbons, for example methylene dichloride or carbon tetrachloride and the like. Benzene and toluene are especially convenient and practical for this use. A variety of suitable acid catalysts may be used for this condensation, for example, the type of catalyst used in a Friedel-Crafts Reaction, i.e. p-toluenesulfonic acid, aluminum chloride, phosphorus pentoxide, boron trifluoride, zinc chloride, hydrochloric acid, perchloric acid, trifluoroacetic acid, sulfuric acid and the like. p-Toluenesulfonic acid, aluminum chloride, boron trifluoride and phosphorus pentoxide are included among the preferred acid catalysts. The amount of acid catalyst used is not especially critical and may range from 0.01 molar equivalents to 100 molar equivalents; however, a range of from 0.1 to 10 molar equivalents is generally preferred. The time of the reaction may range from 10 minutes to 60 hours, with the preferred range being from ½ to 24 hours. The temperature of the reaction may range from −20° C. to the boiling point of the reaction mixture. Preferred temperature ranges include 20° to 120° C.

A more detailed description of the preparation of the above intermediate compounds of formula V and a description of their subsequent conversion to the oxazinoindole derivatives of formula I are disclosed below. For convenience these descriptions are catagorized into sections according to the group selected for Z for the intermediate.

Thereafter these intermediate acids and esters of formula V are converted to compounds of formula I in which $R^1$, $R^2$, $R^3R^4$, $R^5$, $R^6$, $R^7$ and X are defined in the first instance and —$Alk$-$NR^8R^9$ is an amino(lower)alkyl in which Alk is $CH_2$ or $Alk^1$—$CH_2$ wherein $Alk^1$ is as defined in the first instance and $R^8$ and $R^9$ are as defined in the first instance.

In the case where the acid intermediate of formula V is employed, said acid is subjected to amidation by treatment with a lower alkyl chloroformate, preferably ethyl chloroformate, in the presence of triethylamine, affording the corresponding mixed anhydride, which is converted by treatment with the appropriate amine of formula $HNR^8R^9$ in which $R^8$ and $R^9$ are as defined in the first instance, for example, ammonia, methylamine or dimethylamine, to yield the corresponding amide of formula V in which Z is $CONR^8R^9$ or $Alk^1CONR^8R^9$ wherein $Alk^1$, $R^8$ and $R^9$ are as described in the first instance.

a. Preparation and Conversion of Intermediates of Formula V (Z = $COOR^{18}$ and $Alk^1$—$COOR^{18}$)

Intermediates of formula V (Z = $COOR^{18}$ and $Alk^1$—$COOR^{18}$ in which $R^{18}$ is hydrogen or lower alkyl and $Alk^1$ is as defined in the first instance and $R^1$, $R^2$, $R^3$, $R^4$, $R^5$, $R^6$, $R^7$ and X are as defined in the first instance) are readily obtained by the condensation (III + IV → V) by using ketoacid or ketoesters of formula Alternatively, the latter amides are also obtained by treating the ester intermediates of formula V, described above, with the appropriate amine according to known amidation methods, for example, see A. L. F. Beckwith in "The Chemistry of Amides", J. Zalicky, Ed., Interscience Publishers, New York, 1970, pp. 96–105.

Thereafter, the amides so obtained are reduced with a suitable complex metal hydride to yield the desired oxazinolindoles. Examples of suitable complex metal hydrides are lithium aluminum hydride, lithium aluminum hydride-aluminum chloride, aluminum hydride-aluminum chloride, diborane and sodium borohydride-aluminum chloride. Lithium aluminum hydride is preferred.

Two aspects of this latter reduction of the amides are worth noting. The first aspect relates to the reduction of the above amides of formula V in which Z is $CONR^8R^9$ or $Alk^1$—$CONR^8R^9$ wherein $Alk^1$ is as defined in the first instance, $R^8$ is hydrogen and $R^9$ is lower alkyl, i.e. secondary amides, to their corresponding oxazinoindoles of formula I, i.e. secondary amines. In this case a modification of the above process in the following manner is among the preferred procedures. The aforementioned acid or ester intermediate of formula V is reacted with an amine of formula $HNR^8R^9$ in which $R^8$ is benzyl and $R^9$ is lower alkyl corresponding to the $R^9$ of the desired amine. This step is performed according to the amidation step described above. The resulting amide is then reduced with a complex metal hydride according to the above procedures. Thereafter the benzyl group is removed by hydrogenolysis in the presence of a catalyst, preferably 10% palladium on carbon, to afford the desired secondary amine compounds of formula I.

The second aspect relates to a more general modification for the reduction of the above amides of formula V in which Z is $CONR^8R^9$ or $Alk^1$—$CONR^8R^9$ wherein $Alk^1$, $R^8$, and $R^9$ is as defined in the first instance.

This modification is applicable to the reduction of the tertiary, secondary and primary amides and is a preferred modification for the reduction of the latter two. In practising this modification, the aforementioned amide of formula V is treated with triethyloxonium fluoroborate, see R. F. Borch, Tetrahedron Letters, No. 1, 61 (1968), or dimethyl sulfate, see H. Bredereck, et al., Chem. Ber., 98, 2754 (1965), in an inert solvent, for example, methylene dichloride, whereby the corresponding iminoether fluoroborate or methyl sulfate salt is obtained, respectively. Subsequent reduction of the salt thus obtained with a complex metal hydride according to the procedure described above for reducing amides yields the desired oxazinoindole of formula I. Alternatively, the above fluorocarborate or methyl sulfate salt derived from a secondary or primary amide may be decomposed by base treatment, for example, with 10% sodium hydroxide solution or triethylamine, to give the corresponding iminoether derivative which is then reduced in a like manner to the desired oxazinoindole.

When applying the aforementioned steps in the preparation of compounds of formula I in which $R^6$ is hydroxy or lower alkanoyloxy, it is preferable to use corresponding intermediates in which $R^6$ is benzyloky followed by the appropriate transformations as noted previously to yield the desired compounds of formula I.

b. Preparation and Conversion of Intermediates of Formula V (Z = $CONR^8R^9$ and $Alk^1$—$CONR^8R^9$)

The intermediates of formula V in which Z is $CONR^8R^9$ and $Alk^1$—$CONR^8R^9$ wherein $R^8$, $R^9$ and $Alk^1$ are as defined in the first instance, described in the previous section, are also obtained directly by utilizing the appropriate starting materials of formula III and α-, β-, γ-, or δ-ketoamides of formula

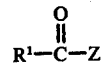

in which $R^1$ is as defined above and Z is $CONR^8R^9$ or $Alk^1$—$CONR^8R^9$ in which $Alk^1$, $R^8$ and $R^9$ are as defined above. The ketoamides required for this condensation are either known, for example, pyruvamide or α,α-dimethylaceto-acetamide, or they may be prepared by known methods, for instance, see "Rodd's Chemistry of the Carbon Compounds", cited above, Vol. 1d, pp. 226–274.

Thereafter these amides of formula V are converted by the reduction process, described above, to the compounds of formula I in which $R^1$, $R^2$, $R^3$, $R^4$, $R^5$, $R^6$, $R^7$ and X are as defined in the first instance and —$Alk$—$NR^8R^9$ is amino(lower)alkyl in which $Alk$ is $CH_2$ or $Alk^1$—$CH_2$ wherein $Alk^1$ is as defined in the first instance and $R^8$ and $R^9$ are as defined in the first instance.

c. Preparation and Conversion of Intermediate of Formula V (Z = $CH_2OCOR^{19}$ and $Alk^1$—$CH_2OCOR^{19}$)

Intermediates of formula V in which Z is $CH_2O$-$COR^{19}$ and $Alk^1$—$CH_2OCOR^{19}$ in which $Alk^1$ and $R^{19}$ are as defined in the first instance, are obtained when a starting material of formula III is condensed with a ketoalcohol lower alkanoic acid ester of formula $R^1COCH_2OCOR^{19}$ or $R^1CO$—$Alk^1$—$CH_2OCOR^{19}$ in which $R^1$, $Alk^1$ and $R^{19}$ are as defined in the first instance in the presence of a suitable acid catalyst according to the conditions described above for the condensation (III + IV → V). The ketoalcohol lower alkyl esters are either known, for example, acetonyl acetate or 5-acetoxy-pentan-2-one, or may be prepared by known methods, for instance, see "Rodd's Chemistry of the Carbon Compounds", cited above, Vol. Id, pp. 49–54.

These intermediates of formula V may then be utilized for the preparation of compounds of formula I of this invention in the following manner. The intermediate is hydrolyzed with an aqueous alcoholic solution of a suitable alkali, for example, sodium hydroxide in aqueous methanol to afford the corresponding primary alcohol. It should be noted that the latter primary alcohols may also be obtained by the direct reduction of the intermediate acids and esters of formula V, described herein in section (a), using a suitable complex metal hydride as described therein. The primary alcohol is then oxidized to the corresponding aldehyde. Although a variety of methods are known for the oxidation of a primary alcohol to its corresponding aldehyde, see for example, "Rodd's Chemistry of the Carbon Compounds", cited above, Vol. 1C, pp. 4–10, we have found that the method of K. E. Pfitzner and J. G. Moffat, J. Am. Chem. Soc., 87, 5670 (1965), using N,N-dicyclohexylcarbodiimide and dimethyl sulfoxide in the presence of a suitable acid, for example, trifluoroacetic acid, is both efficacious and convenient. Thereafter the aldehyde is reacted with an amide of formula $HNR^8R^9$ in which $R^8$ and $R^9$ are as defined in the first instance according to the method of K. N. Campbell, et al., J. Amer. Chem. Soc., 70, 3868 (1948) in the case when the amine used is ammonia or a primary amine, or according to the method of N. J. Leonard and J. V.

Paukstelis, J. Org. Chem., 28, 1397 (1963) when the amine is a secondary amine, to give the corresponding Schiff base or immonium salt, respectively. The product so obtained is reduced with sodium borohydride, see E. Schenker, Angew. Chem., 73, 81 (1961), to yield compounds of formula I in which $R^1$, $R^2$, $R^3$, $R^4$, $R^5$, $R^6$, $R^7$ and X are as defined in the first instance —Alk—$NR^8R^9$ is an amino(lower)alkyl in which Alk is $CH_2$ or $Alk^1$—$CH_2$ wherein $Alk^1$ is as defined in the first instance and $R^8$ and $R^9$ are as defined in the first instance.

Alternatively, the latter compounds of formula I may be obtained by converting the above corresponding alcohol to a reactive intermediate such as the corresponding halide, mesylate or tosylate, which may then be reacted with two or more molar equivalents of an amine of formula $HNR^8R^9$ in which $R^8$ and $R^9$ are as defined in the first instance. Preferably this reaction is performed in a suitable inert solvent, for example, tetrahydrofuran, at 40° to 100° C. or at the boiling point of the reaction mixture for a period of 8 to 24 hours. In connection with alklations of amines of formula $HNR^8R^9$ in which $R^8$ is hydrogen and $R^9$ is lower alkyl as disclosed herein, it is generally more advantageous with respect to yields to perform the alkylation with the corresponding N-benzyl derivative of said amine, i.e., an amine of formula $HNR^8R^9$ in which $R^8$ is benzyl and $R^9$ is lower alkyl. Thereafter, when all appropriate transformation have been performed, the N-benzyl group may be removed by hydrogenolysis with a catalyst, preferably 10% palladium on carbon, to give the desired compounds of formula I.

Alternatively, the above aldehyde is oxidized with a suitable oxidizing agent to yield the corresponding acid intermediates of formula V described in section (a). Although a variety of suitable oxidizing agents may be used for this purpose, for example, silver oxide, alkaline permanganate, hydrogen peroxide, the use of silver oxide according to the method of M. Delépine and P. Bonnet, Compt. rend., 149,39 (1909) is preferred.

Again alternatively, the above aldehyde is converted to its oxime which on reduction with a complex metal hydride yields the corresponding primary amine of formula I in which $R^1$, $R^2$, $R^3$, $R^4$, $R^5$, $R^6$, $R^7$ and X are as defined in the first instance and —Alk—$NR^8R^9$ is an amino(lower)alkyl in which Alk is $CH_2$ or $Alk^1$—$CH_2$ wherein $Alk^1$ is as defined in the first instance and $R^3$ and $R^9$ are hydrogen.

In turn these latter compounds of formula I may be further N-alkylated on the nitrogen of the primary amine with the appropriate lower alkyl halide to the corresponding compounds of formula I in which Y is —Alk—$NR^8R^9$ wherein Alk is $CH_2$ or $Alk^1$—$CH_2$ wherein $Alk^1$ is as defined in the first instance and $R^8$ is hydrogen or lower alkyl and $R^9$ is lower alkyl (i.e. secondary or tertiary amines). In this case depending on the particular derivative desired the N-alkylation may be effected with one or two moles of the alkyl halide to give respectively the secondary or tertiary amine. On the other hand the N-alkylation may be effected in two steps introducing a different alkyl group each time to afford the corresponding tertiary amine in which $R^8$ and $R^9$ are different lower alkyls.

When it is desired to prepare the above tertiary amine compounds in which $R^8$ or $R^9$ are either or both methyl, an alternative alkylation method comprises reacting the appropriate corresponding primary or secondary amine with an aqueous mixture of a substantial excess of formaldehyde and formic acid according to the conditions of the Eschweiler-Clarke reaction, see M. L. Moore, Organic Reactions, 5, 301 (1949), whereby N-methylation is effected.

Another N-alkylation method which may be applied to the above primary and secondary amines involves acylation with a lower alkanoic anhydride or acid halide and subsequent reduction of the resulting amide.

Furthermore, the above primary amines may be used to prepare corresponding compounds of formula I in which $R^8$ and $R^9$ together with the nitrogen atom to which they are joined form a heterocyclic amine radical as defined in the first instance. When used in this manner the primary amines are subjected to known N-alkylation methods, for example, see Method J described by R. B. Moffet, J. Org. Chem., 14, 862 (1949), with the appropriate α,ω-dibromides, for example, tetramethylene dibromide, pentamethylene dibromide, bis(2-chloroethyl)ether, bis(2-chloroethyl)benzylamine followed by hydrogenation in the presence of 10% palladium on carbon to remove the protecting benzyl group, a bis(2-chloroethyl) lower alkylamine or a bis(2-chloroethyl)-N-[hydroxy(lower)alkyl]amine, to give the corresponding desired compound of formula I in which $R^8$ and $R^9$ together with the nitrogen atom to which they are joined form a heterocyclic amine radical, i.e. a pyrrolidino, piperidino, morpholino, piperazino, 4-(lower)alkyl-1-piperazinyl or 4-[hydroxy(lower)alkyl]-1-piperazinyl, respectively.

d. Preparation and Conversion of Intermediates of Formula V (Z = $Alk^2$—L)

Intermediates of formula V in which Z is $Alk^2$—L wherein $Alk^2$ and L are as defined in the first instance, are obtained when a starting material of formula III is condensed with a β, γ or δ-haloketone of formula $R^1CO$—$Alk^2$—L in which $R^1$, $Alk^2$ and L are as defined in the first instance in the presence of a suitable acid catalyst according to the conditions described above for the condensation (III + IV → V). The haloketones are either known, for example, 4-chlorobutan-2-one, or they may be prepared by known methods, for instance, see "Rodd's Chemistry of Carbon Compounds", cited above, Vol. lc., pp. 70–71 and "Methoden der Organischen Chemie", Houben-Weyl, E. Muller, Ed., Vol V/3, Georg Thieme Verlag, Stuttgart 1962, pp. 511–1076.

Thereafter these intermediates of formula V are treated with a two molar excess of an amine of formula $HNR^8R^9$ in which $R^8$ and $R^9$ are as defined in the first instance to yield the compounds of formula I in which $R^1$, $R^2$, $R^3$, $R^4$, $R^5$, $R^6$, $R^7$ and X are as described in the first instance, and —Alk—$NR^8R^9$ is an amino(lower)alkyl in which Alk is $Alk^2$ as defined in the first instance and $R^8$ and $R^9$ are as defined above. Preferably this reaction is performed in a suitable inert solvent, for example, tetrahydrofuran at the boiling point of the reaction mixture for a period of 8 to 24 hours.

e. Preparation and Conversion of Intermediates of Formula V (Z = $AlkNR^8COR^{20}$)

Intermediates of formula V in which Z is $AlkNR^8COR^{20}$ wherein Alk, $R^8$ and $R^{20}$ are as defined in the first instance are readily obtained by the condensation (III + IV → V) by using ketoamides of formula

in which $R^1$, Alk, $R^8$ and $R^{20}$ are as defined in the first instance together with the appropriate starting material of formula III.

The ketoamides used herein are either known, for example, formamidoacetone [A. Treibs and W. Sutter, Chem. Ber., 84, 96 (1951)], see also R. H. Wiley and O. H. Borum, J. Amer. Chem. Soc., 70, 2005 (1948), or may be prepared by known procedures, for example, see "Methoden der Organischen Chemie", cited above, Vol. XI/1, 1957, especially pp. 58–62, 285–289 and 508–509, and F. F. Blicke, Organic Reactions, 1, 303 (1942).

Thereafter, reduction with a complex metal hydride converts the instant intermediates of formula V to oxazinoindoles of formula I in which $R^1$, $R^2$, $R^3$, $R^4$, $R^5$, $R^6$, $R^7$, and X are as described in the first instance, and —Alk—$NR^8R^9$ is an amino(lower)alkyl in which Alk and $R^8$ are as defined in the first instance and $R^9$ is lower alkyl.

f. Preparation and Conversion of Intermediates of Formula V (Z = Alk — $NO_2$)

Intermediates of formula V in which Z is Alk—$NO_2$ where Alk is as defined in the first instance, are obtained by the condensation (III + IV → V) when the starting materials of formula III and appropriate α-, β-, γ-, and δ-nitroketones of formula

in which $R^1$ and Alk are as defined in the first instance are employed therein in the presence of a suitable acid catalyst. In this case trifluoroacetic acid is the preferred acid catalyst.

The nitroketones used herein are either known, for example, 1-nitro-2-propanone, N. Levy and C. W. Scaife, J. Chem. Soc., 1100, (1946) and 5-nitro-2-hexanone, H. Shechter, et al., J. Amer. Chem. Soc. 74, 3664 (1952) or they may be prepared by known methods, for example, see Levy and Scaife, cited above, Shechter, et al. cited above, "Rodd's Chemistry of Carbon Compounds", cited above, Vol. lc, pp. 71–72 and "Methoden der Organischen Chemie", cited above, Vol. X/1, 1971, p. 203.

Thereafter, these intermediates of formula V are reduced with a complex metal hydride, preferably lithium aluminum hydride, to afford the oxazinoindoles of formula I in which $R^1$, $R^2$, $R^3$, $R^4$, $R^5$, $R^6$, $R^7$ and X are as defined in the first instance, and —Alk—$NR^8R^9$ is an amino(lower)alkyl in which Alk is defined in the first instance and $R^8$ and $R^9$ are hydrogen.

If desired the latter compounds may be N-alkylated according to the methods described in section (c) to give the compounds of formula I in which $R^1$, $R^2$, $R^3$, $R^4$, $R^5$, $R^6$, $R^7$ and X are as defined in the first instance and Alk—$NR^8R^9$ is an amino(lower)alkyl in which Alk, $R^8$ and $R^9$ are as defined in the first instance.

The following examples illustrate further this invention.

EXAMPLE 1

3-Methylindole-1-ethanol(III: $R^2$, $R^3$, $R^4$, $R^5$ and $R^6$ = H, $R^7$ = $CH_3$ and $X^1$ = OH)

Procedure A:

Commercial n-butyl lithium in hexane (3.05 mole) is diluted with 1000 ml of dry tetrahydrofuran (THF). To this cooled (−10° to 0° C) solution the starting material of formula II, skatole (393 g, 3.0 mole) in 1000 ml of dry THF, is added dropwise. The reaction is stirred at the same low temperature for 1 hour and then 300 ml of ethylene oxide in 300 ml of dry THF is added to the mixture. The temperature of the reaction is allowed to rise to room temperature and at this temperature the reaction is stirred overnight.

THF is evaporated and the residue is dissolved in methylene chloride and washed with concentrated HCl. The methylene chloride solution is then washed with 10% sodium bicarbonate, water and dried ($MgSO_4$). The solvent is evaporated and the product distilled at reduced pressure to give the title compound, b.p. 124° C/0.25 mm.

Procedure B:

The starting material of formula II, skatole (35 g, 0.276 mole) in 300 ml of dimethylformamide (DMF) is added dropwise to stirred mixture of sodium hydride (14.0 g, 55% oil dispension) in 325 ml of DMF. The mixture is heated at 40° C for 2 hours. After cooling in an ice-water bath ethyl bromoacetate (116.5 g, 0.7 mole) is added dropwise keeping the temperature below 20° C. After the addition, stirring is continued for 5 minutes, and then water added cautiously to destroy any excess hydride. The reaction mixture is partitioned between water and ether. The ether layer washed with water, dried ($MgSO_4$) and evaporated under reduced pressure.

The residue, 3-methyl-indole-1-acetic acid ethyl ester, is dissolved in 900 ml of methanol, potassium hydroxide (90g) in 400 ml of 1:1 methanol-$H_2O$ is then added. The mixture is stirred at room temperature for 1½ hours. The methanol is evaporated under reduced pressure. The residue is diluted with water (800 ml) and extracted (3x) with ether. Acidification with 6N HCl of the aqueous phase yields 3-methyl-indole-1-acetic acid, m.p. 174°–176° C.

The latter compound (47.5 g., 0.25 mole) in 1000 ml of ether is slowly added to a stirred mixture of lithium aluminum hydride (12.5 g) (0.32 moles) in 700 ml of ether. The reaction is kept below 15° C using an ice-water bath. The reaction is stirred for 15 minutes after the addition, the excess hydride destroyed with water, and the precipitate collected. The ether filtrate is washed with water, dried over sodium sulfate and evaporated under reduced pressure to afford an oil. Chromatography on silica gel using 15% ethylacetate in benzene as eluant gives the title compound, identical with the product of procedure A.

By following the procedure A of Example 1 other indole-1-ethanol intermediates of formula III for example those listed in Examples 6 to 55, may be prepared by the appropriate choice of the starting material of formula II and ethylene oxide derivative. For example, by replacing skatole and ethylene oxide with equivalent amounts of 3,7-dimethylindole, R. Robinson et al., cited above, and 3,3-dimethyl-1,2-epoxybutane, V. Franzen and H. E. Driesen, cited above, respectively, a mixture of β-isopropyl-α,3,7-trimethyl-indole-1- ethanol and α-isopropyl-β,3,7-trimethyl-indole-1-ethanol, are obtained. Such mixtures of positional isomers may be separated by fractional distillation, fractional recrystallization or chromatography. Likewise, the replacement of skatole with 3-isopropylindole, R. Robinson et al. cited above, in procedure A of Example 1 yields 3-isopropylindole-1-ethanol.

By following procedure B of Example 1 other indole-1-ethanol intermediates of formula III in which $R^2$ and $R^3$ are hydrogen may be prepared by the appropriate choice of the starting material of formula II and α-haloacetic acid lower alkyl ester of formula $LCR^4R^5COO$-(lower alkyl) in which L is halo and $R^4$ and $R^5$ are hydrogen or lower alkyl. For example, by replacing skatole and ethyl bromoacetate with equivalent amounts of 3-ethylindole, R. Robinson et al., cited above, and 2,3-epoxybutane, F. G. Bordwell and P. S. Landis, J. Amer. Chem. Soc., 79, 1593 (1957), respectively, α,β-dimethyl-3-ethyl-indole-1-ethanol is obtained. Likewise the replacement of skatole with 3-butylindole, R. Robinson et al., cited above, in the procedure B of Example 1 yields 3-butylindole-1-ethanol.

EXAMPLE 2

3-Methylindole-1-ethanethiol (III: $R^2$, $R^3$, $R^4$, $R^5$ and $R^6$ = H, $R^7$ = $CH_3$ and $X^1$ = SH)

Procedure A:

N,N-dicyclohexylcarbodiimide (9.0 g) is added to a cooled, stirred solution of 3-methylindole-1-ethanol (3.0 g) in 30 ml of dimethyl sulfoxide-benzene (2:1) containing trifluoroacetic acid (0.6 ml) and pyridine (1.12 ml). The reaction is stirred at room temperature under nitrogen for 5 hours. The reaction mixture is now diluted with 300 ml of ether, followed by the dropwise addition of a solution of oxalic acid (3.78 g) in 11 ml of methanol. After 30 minutes, water (300 ml) is added and the insoluble material is collected. The organic phase is washed with water (2X), 5% aqueous sodium bicarbonate (2X) and water (2X). After drying (MgSO$_4$) the organic phase is evaporated to yield 3-methylindole-1-acetaldehyde. The latter compound is then converted to its corresponding gem-dithiol with hydrogen sulfide and reduced with lithium aluminium hydride according to the method of T. L. Cairns et al., J. Amer. Chem. Soc., 74, 3982 (1952), to yield the title compound, $\gamma_{max}^{CHCl_3}$ 2570 cm$^{-1}$.

Procedure B:

To a stirred solution of 7.2 g of 3-methylindole-1-ethanol, described in Example 1, in 500 ml. of dry ether (ice bath) is slowly added 1.2 ml of phosphorus tribromide in 100 ml of dry ether. A dark red oily complex separates. The reaction mixture is stirred 36–48 hours at room temperature, then decomposed with ice and water. The separated ether-layer is quickly washed with a 10% solution of sodium bicarbonate and with water again, dried over calcium chloride for 2 min., decanted, and dried over magnesium sulfate for 30 min. The filtrate is evaporated yielding 1-(2-bromoethyl)-3-methylindole.

A solution of 10.4 g. of sodium thiosulfate in 60 ml. of water and 100 ml. of ethanol is poured onto 8.6 g. of 1-(2-bromoethyl)-3-methylindole. The reaction mixture is stirred and heated at reflux for 3.5 hr., allowed to cool, and evaporated to dryness. The solid residue is dissolved in boiling isopropanol, dried with a hydrated alkali-aluminum silicate ("Molecular Sieves"), and filtered. Chilling of the filtrate causes 6.4 g. of the sodium indolyethyl thiosulfate derivative to precipitate. This material is collected by filtration and washed with ether. The isolated intermediate is heated at reflux with a solution of sodium hydroxide (9 g. of NaOH, 60 ml. of water, 140 ml. of ethanol) for 3 hr. Ethanol is removed under reduced pressure, the aqueous residue diluted with water and extracted with three portions of ether. Combined ether extracts are washed with water, saturated brine solution, and dried over magnesium sulfate. The filtrate is evaporated, to yield bis-[2-(3-methylindol-1-yl)ethyl]disulfide.

The latter product (1.4 g.) in 100 ml. of dry ether is dropped into a stirred suspension of 600 mg. LiAlH$_4$ in 80 ml. of dry ether. The reaction mixture is heated to reflux for 3 hr. and then kept for 15 hr. at room temperature. Decomposition with 2.8 ml. of water is carried out in a stream of nitrogen. After 60 min. of stirring, a white precipitate is filtered off with suction, the cake was washed with ether, and the filtrate dried over magnesium sulfate. The clear ether solution is evaporated to give the title compound.

By following procedure A or B of Example 2 other indole-1-ethanethiol intermediates of formula III, for example those described in Examples 57 to 106 may be prepared by the appropriate choice of indole-1-ethanol intermediates of formula III. For example, by replacing 3-methylindole-1-ethanol with an equivalent amount of β-isopropyl-α,3,7-trimethylindole-1-ethanol, β-isopropyl-α,3,7-trimethyl-indole-1-ethanethiol is obtained. Likewise, by replacing 3-methylindole-1-ethanol with an equivalent amount of 3-isopropylindole-1-ethanol, 3-isopropylindole-1-ethanethiol is obtained.

EXAMPLE 3

3,4-Dihydro-1,10-dimethyl-1H-1,4-oxazino[4,3-a]indole-1-acetic acid (V; $R^1$ and $R^7$ = $CH_3$, $R^2$, $R^3$, $R^4$, $R^5$ and $R^6$ = H, X = O and Z = $CH_2COOH$)

A mixture of the intermediate of formula III, 3-methylindole-1-ethanol (26.5 g., 0.15 mole), described in Example 1, in toluene (600 ml.), ethyl acetoacetate (36 g., 0.20 mole) and p-toluenesulfonic acid (2.0 g.) is heated at reflux for 6 hr. using a water separator. The toluene solution is washed with water, 5% bicarbonate solution, and again with water. The solution is then dried over sodium sulfate and the solvent evaporated under reduced pressure to give an oil. The oil was subjected to chromatograhy on silica gel. Elution with 10% ethyl acetate is benzene and concentration of the eluate affords the ester, 3,4-dihydro-1,10-dimethyl-1H-1,4-oxazino[4,3-a]indole-1-acetic acid ethyl ester, as an oil, $\gamma_{max}^{film}$ 1725 cm$^{-1}$.

Hydrolysis of this ester to the title compound is effected as follows: The ester (39.9 g.) is dissolved in 800 ml. of methanol containing 22.5 g. of KOH in 20 ml. of water. After stirring for 5 hr. at 50° C. and for 12 hr. at room temperature, the solvent is evaporated under reduced pressure. The residue is taken into water and washed twice with ether, acidified with 6N HCl and extracted with ether. The ether solution is washed once with water, dried (Na$_2$SO$_4$) and evaporated under reduced pressure to afford a solid. The solid is recrystallized from petroleum ether to afford the title compound, m.p. 138°–139° C., nmr (CDCl$_3$) $\gamma$1.75 (s, 3H), 2.86 and 3.18 (d, J = 14.5 cps, 2H), 4.07 (m, 4H).

An equivalent amount of methyl acetoacetate may replace ethyl acetoacetate in the procedure of this Example. In this case, 3,4-dihydro-1,10-dimethyl-1H-1,4-oxazino[4,3-a]-indole-1-acetic acid methyl ester is obtained as the ester.

An equivalent amount of propyl acetoacetate may replace ethyl acetoacetate in the procedure of this Example. In this case, 3,4-dihydro-1,10-dimethyl-1H-1,4-oxazino[4,3-a]-indole-1-acetic acid propyl ester is obtained as the ester.

EXAMPLE 4

1,10-Dimethyl-3,4-dihydro-1H-oxazino[4,3-a]-indole-1-propionic acid (V; $R^1$ and $R^7 = CH_3$, $R^2$, $R^3$, $R^4$, $R^5$ and $R^6 = H$, $X = O$ and $Z = CH_2CH_2COOH$)

Procedure A

A mixture of the intermediate of formula III, 3-methylindole-1-ethanol (29.7 g., 0.17 mole), described in Example 1, ethyl levulinate (26.96 g., 0.187 mole) and p-toluenesulfonic acid (2.25 g.) in dry benzene (650 ml.) is refluxed with stirring for 12 hr. with hydrated alkali-aluminum silicate (Molecular Sieves No. 4). The benzene solution is washed with 5% aqueous $NaHCO_3$, followed by water. Concentrations of the solution gave a residue, which is passed through a silica gel column using 15% ethyl acetate in benzene to afford the ester, 3,4-dihydro-1,10-dimethyl-1H-1,4-oxazino[4,3-a]indole-1-propionic acid ethyl ester, as an oil, $\gamma_{maxCHCl_3}$ 1730 cm$^{-1}$.

This ester (41.9 g.) is dissolved in 650 ml. of methanol containing 23 g. of KOH in 50 ml. of water and heated at 50° C. for 1 hr. The solvent is evaporated and the residue taken into water. The aqueous mixture is washed with ether twice, acidified with 6N HCl and extracted three times with ether. The ether solution is washed once with water, dried over $MgSO_4$ and evaporated, under reduced pressure to yield a solid. The solid is recrystallized from ethyl acetate-petroleum ether to give the title compound, m.p. 115°–116° C., nmr (CDCl$_3$) δ1.62 (s, 3H), 2.30 (m, 7H), 4.04 (4H), 7.21–7.52 (m, 4H), 10.93 (1H).

Procedure B:

A mixture of the intermediate of formula III, 5-methylindole-1-ethanol (500 mg.), levulinic acid (580 mg.), 75 ml. of benzene, 1.7 g. of phosphorous pentoxide and about 0.5 g. of diatomaceous earth (Celite) is stirred magnetically at room temperature for 15 min. and then at 70° C. for 1½ hr. The reaction mixture is filtered. The filtrate is washed three times with 5N NaOH; the combined aqueous phase is washed twice with ether and then rendered acidic with cold 50% HCl. The aqueous phase is extracted with chloroform. The chloroform extract is dried (Na$_2$SO$_4$) and evaporated to dryness. Recrystallization of residue from ethyl acetate-petroleum ether affords the title compound, identical to the produce of procedure A of this Example.

The procedure of Example 3 and 4 (Procedure A) may be followed to prepare other intermediates of formula V in which $R^1$, $R^2$, $R^3$, $R^4$, $R^5$, $R^6$, $R^7$, X are as defined in the first instance and Z is COOR$^{10}$ or Alk$^1$—COOR$^{10}$ wherein R$^{10}$ and Alk$^1$ are as defined in the first instance. Examples of such compounds are listed in Tables I and II. In each of these instances intermediate of formula III and ketoester listed therein are used in an equivalent amount to the intermediates of formula III and ketoesters listed in Examples 3 and 4 (Procedure A). Note that in each of these instances an ester is obtained prior to hydrolysis. This ester is the corresponding intermediate of formula V in which Z is COOR$^{18}$ or Alk$^1$—COOR$^{18}$ wherein R$^{18}$ is lower alkyl and Alk$^1$ is defined in the first instance, the alkyl portion of said ester being derived from the R$^{18}$ portion of the ketoester of formula IV employed therein.

Likewise, the procedure of Example 4 (Procedure B) may be used to prepare the products listed in Tables I and II except that in this case an equivalent amount of the corresponding ketoacid of formula IV is used instead of the ketoester listed in the table.

TABLE I

| EXAMPLE | INTERMEDIATE OF FORMULA III IN WHICH $X^1$ IS OH | | | | | | KETOESTER OF FORMULA IV, $R^1$—$\overset{\overset{O}{\|}}{C}$—Alk$^1$—CO—OR$^{10}$ | | | PRODUCT: (PREFIX LISTED BELOW)-3,4-DIHYDRO-1H-1,4-OXAZINO[4,3-a]INDOLE-1-(SUFFIX LISTED BELOW) | |
|---|---|---|---|---|---|---|---|---|---|---|---|
| | $R^2$ | $R^3$ | $R^4$ | $R^5$ | $R^6$ | $R^7$ | $R^1$ | Alk$^1$—CO | | $R^{10}$ | PREFIX//SUFFIX |
| 5 | H | H | H | H | H | CH$_3$ | CH$_3$ | CO | | C$_2$H$_5$ | 1,10-dimethyl//carboxylic acid |
| 6 | CH$_3$ | H | H | H | H | CH$_3$ | C$_2$H$_5$ | CO | | C$_2$H$_5$ | 1-ethyl-3,10-dimethyl//carboxylic acid |
| 7 | n-C$_3$H$_7$ | H | H | H | 5-CH$_3$ | CH$_3$ | n-C$_3$H$_7$ | CO | | CH$_3$ | 1,3-diisopropyl-8,10-dimethyl//carboxylic acid |
| 8 | CH$_3$ | CH$_3$ | H | H | 5-OH | CH$_3$ | CH$_3$ | CO | | CH$_3$ | 8-hydroxy-1,3,3,10-tetramethyl//carboxylic acid |
| 9 | H | H | H | H | 7-C$_2$H$_5$ | C$_2$H$_5$ | n-C$_3$H$_7$ | CO | | CH$_3$ | 6,10-diethyl-1-propyl//carboxylic acid |
| 10 | H | H | i-C$_3$H$_7$ | H | H | i-C$_3$H$_7$ | △ | CO | | CH$_3$ | 1-cyclopropyl-4,10-diisopropyl//carboxylic acid |
| 11 | CH$_3$ | CH$_3$ | C$_2$H$_5$ | C$_2$H$_5$ | H | C$_2$H$_5$ | ◯ | CO | | CH$_3$ | 1-cyclopentyl-4,4,10-triethyl-3,3-dimethyl//carboxylic acid |
| 12 | H | H | CH$_3$ | H | H | CH$_3$ | CH$_3$ | CH$_2$CO | | C$_2$H$_5$ | 1,4,10-trimethyl//acetic acid |
| 13 | H | H | H | H | H | CH$_3$ | C$_2$H$_5$ | CH$_2$CO | | C$_2$H$_5$ | 1-ethyl-10-methyl//acetic acid |
| 14 | H | H | H | H | H | CH$_3$ | n-C$_3$H$_7$ | CH$_2$CO | | C$_2$H$_5$ | 10-methyl-1-propyl//acetic acid, m.p. 146 – 148° C. |
| 15 | H | H | H | H | H | CH$_3$ | i-C$_3$H$_7$ | CH$_2$CO | | C$_2$H$_5$ | 1-isopropyl-10-methyl//acetic acid |

TABLE I-continued

| EXAMPLE | INTERMEDIATE OF FORMULA III IN WHICH $X^1$ IS OH | | | | | KETOESTER OF FORMULA IV, $R^1-\overset{\overset{O}{\|}}{C}-Alk^1-CO-OR^{10}$ | | | | PRODUCT: (PREFIX LISTED BELOW)-3,4-DIHYDRO-1H-1,-4-OXAZINO[4,3-a]INDOLE-1-(SUFFIX LISTED BELOW) | |
|---|---|---|---|---|---|---|---|---|---|---|---|
| | $R^2$ | $R^3$ | $R^4$ | $R^5$ | $R^6$ | $R^7$ | $R^1$ | $Alk^1$—CO | $R^{10}$ | PREFIX//SUFFIX | |
| 16 | $CH_3$ | H | H | H | H | $CH_3$ | $n-C_3H_7$ | $CH_2CO$ | $C_2H_5$ | 3,10-dimethyl-1-propyl//acetic acid | |
| 17 | $CH_3$ | H | $C_2H_5$ | $CH_3$ | H | $CH_3$ | $C_2H_5$ | $CH_2CO$ | $C_2H_5$ | 1,4-diethyl-3,10-dimethyl//acetic acid | |
| 18 | H | H | H | H | H | $CH_3$ | $CH_3$ | $CH(CH_3)CO$ | $C_2H_5$ | α,1,10-trimethyl//acetic acid | |
| 19 | H | H | H | H | H | $C_2H_5$ |  | $C(CH_3)_2CO$ | $C_2H_5$ | 1-cyclohexyl-10-ethyl-α,α-dimethyl//acetic acid | |
| 20 | H | H | H | H | H | $CH_3$ | $t-C_4H_9$ | $CH_2CO$ | $C_2H_5$ | 1-t-butyl-10-methyl//acetic acid | |
| 21 | H | H | H | H | H | $CH_3$ | $n-C_4H_9$ | $CH_2CO$ | $C_2H_5$ | 1-butyl-10-methyl//acetic acid | |
| 22 | H | H | H | H | 7-$CH_3$ | $C_2H_5$ | $n-C_3H_7$ | $CH_2CO$ | $C_2H_5$ | 10-ethyl-6-methyl-1-propyl//acetic acid | |
| 23 | H | H | H | H | 5-Br | $C_2H_5$ | $C_2H_5$ | $CH_2CO$ | $C_2H_5$ | 8-bromo-1,10-diethyl//acetic acid | |
| 24 | H | H | H | H | 5-$OCH_3$ | $n-C_4H_9$ | $CH_3$ | $CH_2CO$ | $CH_3$ | 10-butyl-8-methoxy-1-methyl//acetic acid | |
| 25 | H | H | H | H | 5-$OCOCH_3$ | $t-C_4H_9$ | $CH_3$ | $CH_2CO$ | $C_2H_5$ | 8-acetoxy-10-t-butyl-1-methyl//acetic acid | |
| 26 | H | H | H | H | 5-benzyloxy | $i-C_3H_7$ | $CH_3$ | $CH_2CO$ | $C_2H_5$ | 8-benzyloxy-10-isopropyl-1-methyl//acetic acid | |
| 27 | H | H | H | H | 4-$CH_3$ | $CH_3$ | $n-C_3H_7$ | $CH_2CO$ | $C_2H_5$ | 9,10-dimethyl-1-propyl//acetic acid | |
| 28 | H | H | H | H | 6-$CH_3$ | $CH_3$ | $n-C_3H_7$ | $CH_2CO$ | $C_2H_5$ | 7,10-dimethyl-1-propyl//acetic acid | |
| 29 | H | H | H | H | 5-$NO_2$ | $n-C_3H_7$ | $n-C_3H_7$ | $CH_2CO$ | $C_2H_5$ | 8-nitro-1,10-dipropyl//acetic acid | |
| 30 | H | H | $CH_3$ | $CH_3$ | H | $CH_3$ | $n-C_3H_7$ | $CH_2CO$ | $C_2H_5$ | 4,4,10-trimethyl-1-propyl//acetic acid | |
| 31 | $CH_3$ | $CH_3$ | H | H | 5-$OC_2H_5$ | $C_2H_5$ |  | $CH(C_2H_5)CO$ | $C_2H_5$ | 1-cyclopropyl-α,α,10-triethyl-3,3-dimethyl-8-ethoxy//acetic acid | |
| 32 | $CH_3$ | $CH_3$ | $C_2H_5$ | $C_2H_5$ | 6-$C_2H_5$ | $n-C_4H_9$ |  | $C(CH_3)_2CO$ | $C_2H_5$ | 10-butyl-1-cyclohexyl-α,α,3,3-tetramethyl-,4,7-triethyl//acetic acid | |
| 33 | $CH_3$ | H | $n-C_3H_7$ | $n-C_3H_7$ | 4-$n-C_3H_7$ | $CH_3$ | $C_2H_5$ | $CH(CH_3)CO$ | $C_2H_5$ | 1-ethyl-α,3,10-trimethyl-4,4,9-tripropyl//acetic acid | |
| 34 | H | H | H | H | H | $C_2H_5$ | $n-C_3H_7$ | $C(CH_3)_2CO$ | $C_2H_5$ | α,α-dimethyl-10-ethyl-1-propyl//acetic acid | |
| 35 | $C_2H_5$ | $C_2H_5$ | $C_2H_5$ | $C_2H_5$ | 4-$C_2H_5$ | $C_2H_5$ | $t-C_4H_9$ | $C(i-C_3H_7)_2CO$ | $C_2H_5$ | 1-t-butyl-α,α-diisopropyl-3,3,4,4,9,10-hexaethyl//acetic acid | |
| 36 | H | H | H | H | 4-I | $CH_3$ | $i-C_3H_7$ | $CH_2CH_2CO$ | $C_2H_5$ | 10-methyl-9-iodo-1-isopropyl//propionic acid | |
| 37 | $CH_3$ | $CH_3$ | $CH_3$ | $CH_3$ | 7-$OCOCH_3$ | $C_2H_5$ | $C_2H_5$ | $CH_2CH(CH_3)CO$ | $C_2H_5$ | 6-acetoxy-1,10-diethyl-α,3,3,4,4-pentamethyl//propionic acid | |
| 38 | H | H | H | H | 6-OH | $CH_3$ | $n-C_3H_7$ | $CH_2C(C_2H_5)_2CO$ | $C_2H_5$ | β,β-diethyl-7-hydroxy-10-methyl-1-propyl//propionic acid | |
| 39 | $CH_3$ | H | H | H | 7-$NO_2$ | $CH_3$ |  | $CH(n-C_3H_7)CH_2CO$ | $C_2H_5$ | 1-cyclobutyl-3,10-dimethyl-6-nitro-α-propyl//propionic acid | |
| 40 | H | H | $CH_3$ | H | 5-$CH_3$ | $CH_3$ |  | $C(CH_3)_2C(CH_3)_2CO$ | $C_2H_5$ | 1-cyclopropyl-α,α,β,β,4,-8,10-heptamethyl//propionic acid | |
| 41 | $CH_3$ | H | H | H | H | $CH_3$ | $CH_3$ | $CH_2C(n-C_3H_7)_2CO$ | $C_2H_5$ | 1,3,10-trimethyl-α,α-dipropyl//propionic acid | |
| 42 | $CH_3$ | H | $C_2H_5$ | $C_2H_5$ | H | $CH_3$ | $C_2H_5$ | $CH(CH_3)C(CH_3)_2CO$ | $CH_3$ | α,α,β,3,10-pentamethyl-1,4,4-triethyl//propionic acid | |
| 43 | H | H | $CH_3$ | $CH_3$ | H | $C_2H_5$ | $C_2H_5$ | $C(CH_3)_2CH_2CO$ | $CH_3$ | 1,10-diethyl-β,β,4-tetramethyl//propionic acid | |
| 44 | H | H | $n-C_3H_7$ | H | 4-$OCOC_2H_5$ | $CH_3$ |  | $C(C_2H_5)_2C(C_2H_5)_2CO$ | $CH_3$ | 1-cyclopentyl-10-methyl-9-propionoxy-4-propyl-α,β,β-triethyl//propionic acid | |
| 45 | $n-C_3H_7$ | H | H | H | 4-$OCH_3$ | $CH_3$ | $n-C_3H_7$ | $CH_2CH(CH_3)CO$ | $C_2H_5$ | α,10-dimethyl-1,3-dipropyl-9-methoxy//propionic acid | |
| 46 | $C_2H_5$ | H | H | H | 5-$NO_2$ | $CH_3$ | $CH_3$ | $C(C_2H_5)_2C(C_2H_5)_2CO$ | $C_2H_5$ | 1,10-dimethyl-8-nitro-α,α,β,β,3-pentaethyl//propionic acid | |
| 47 | $C_2H_5$ | $C_2H_5$ | H | H | 4-$C_2H_5$ | $CH_3$ | $n-C_3H_7$ | $CH(n-C_3H_7)CH_2CO$ | $CH_3$ | β,1-dipropyl-3,3,9,10-tetraethyl//propionic acid | |

TABLE I-continued

| EXAMPLE | INTERMEDIATE OF FORMULA III IN WHICH $X^1$ IS OH | | | | | | KETOESTER OF FORMULA IV, $R^1-\overset{O}{\underset{\|}{C}}-Alk^1-CO-OR^{10}$ | | | PRODUCT: (PREFIX LISTED BELOW)-3,4-DIHYDRO-1H-1,4-OXAZINO[4,3-a]INDOLE-1-(SUFFIX LISTED BELOW) |
|---|---|---|---|---|---|---|---|---|---|---|
| | $R^2$ | $R^3$ | $R^4$ | $R^5$ | $R^6$ | $R^7$ | $R^1$ | $Alk^1-CO$ | $R^{10}$ | PREFIX//SUFFIX |
| 48 | H | H | H | H | 6-$OC_2H_5$ | $C_2H_5$ | cyclopropyl | $CH(C_2H_5)CH(C_2H_5)CO$ | $C_2H_5$ | 1-cyclopropyl-7-ethoxy-$\alpha,\beta$,10-triethyl//propionic acid |
| 49 | H | H | H | H | H | $CH_3$ | $CH_3$ | $CH_2CH_2CH_2CO$ | $C_2H_5$ | 1,10-dimethyl//butyric acid |
| 50 | $CH_3$ | H | H | H | H | $CH_3$ | $C_2H_5$ | $CH(CH_3)CH_2CH_2CO$ | $C_2H_5$ | 1-ethyl-$\gamma$,3,10-trimethyl butyric acid |
| 51 | $CH_3$ | $CH_3$ | H | H | H | $CH_3$ | n-$C_3H_7$ | $C(C_2H_5)_2CH_2CH_2CO$ | $C_2H_5$ | $\gamma,\gamma$-diethyl-1-propyl-3,3,10-trimethyl//butyric acid |
| 52 | $C_2H_5$ | H | H | H | 6-$NO_2$ | $C_2H_5$ | n-$C_4H_9$ | $[C(CH_3)_2]_3CO$ | $C_2H_5$ | 1-butyl-3,10-diethyl-7-nitro-$\alpha,\beta,\gamma$-trimethyl//butyric acid |
| 53 | $CH_3$ | $CH_3$ | H | H | 4-n-$C_3H_7$ | n-$C_3H_7$ | n-$C_3H_7$ | $CH_2[CH(C_2H_5)]_2CO$ | $C_2H_5$ | $\alpha,\beta$-diethyl-3,3-dimethyl 1,9,10-tripropyl//butyric acid |
| 54 | H | H | H | H | 7-OH | n-$C_4H_9$ | $C_2H_5$ | $C(CH_3)_2CH_2C(CH_3)_2CO$ | $C_2H_5$ | 10-butyl-1-ethyl-6-hydroxy-$\alpha,\alpha,\gamma,\gamma$-tetramethyl//butyric acid |
| 55 | $CH_3$ | H | $CH_3$ | H | 4-$OC_2H_5$ | t-$C_4H_9$ | $C_2H_5$ | $[C(CH_3)_2]_3CO$ | $C_2H_5$ | 10-t-butyl-9-ethoxy-1-ethyl-$\alpha,\alpha,\beta,\beta,\gamma,\gamma$,3,4-octomethyl//butyric acid |

TABLE II

| Ex. | INTERMEDIATE OF FORMULA III IN WHICH $X^1$ IS SH | | | | | | KETOESTER OF FORMULA IV, $R^1-\overset{O}{\underset{\|}{C}}-Alk^1-CO-OR^{10}$ | | | PRODUCT: (PREFIX LISTED BELOW)-3,4-DIHYDRO-1H-1,4-THIAZINO-[4,3-a]INDOLE-1-(SUFFIX LISTED BELOW) |
|---|---|---|---|---|---|---|---|---|---|---|
| | $R^2$ | $R^3$ | $R^4$ | $R^5$ | $R^6$ | $R^7$ | $R^1$ | $Alk^1$-CO | $R^{10}$ | PREFIX//SUFFIX |
| 56 | H | H | H | H | H | $CH_3$ | $CH_3$ | CO | $C_2H_5$ | 1,10-dimethyl//carboxylic acid |
| 57 | $CH_3$ | H | H | H | H | $CH_3$ | $C_2H_5$ | CO | $C_2H_5$ | 1-ethyl-3,10-dimethyl//carboxylic acid |
| 58 | n-$C_3H_7$ | H | H | H | 5-$CH_3$ | $CH_3$ | n-$C_3H_7$ | CO | $CH_3$ | 1,3-diisopropyl-3,10-methyl//carboxylic acid |
| 59 | $CH_3$ | $CH_3$ | H | H | 5-OH | $CH_3$ | $CH_3$ | CO | $CH_3$ | 8-hydroxy-1,3,3,10-tetramethyl//carboxylic acid |
| 60 | H | H | H | H | 7-$C_2H_5$ | $C_2H_5$ | n-$C_3H_7$ | CO | $CH_3$ | 6,10-diethyl-1-propyl//carboxylic acid |
| 61 | H | H | i-$C_3H_7$ | H | H | i-$C_3H_7$ | cyclopropyl | CO | $CH_3$ | 1-cyclopropyl-4,10-diisopropyl//carboxylic acid |
| 62 | $CH_3$ | $CH_3$ | $C_2H_5$ | $C_2H_5$ | H | $C_2H_5$ | cyclopentyl | CO | $CH_3$ | 1-cyclopentyl-4,4,10-triethyl-3,3-dimethyl//carboxylic acid |
| 63 | H | H | H | H | H | $CH_3$ | $CH_3$ | $CH_2CO$ | $C_2H_5$ | 1,10-dimethyl//acetic acid |
| 64 | H | H | H | H | H | $CH_3$ | $C_2H_5$ | $CH_2CO$ | $C_2H_5$ | 1-ethyl-10-methyl//acetic acid |
| 65 | H | H | H | H | H | $CH_3$ | n-$C_3H_7$ | $CH_2CO$ | $C_2H_5$ | 10-methyl-1-propyl//acetic acid |
| 66 | H | H | H | H | H | $CH_3$ | i-$C_3H_7$ | $CH_2CO$ | $C_2H_5$ | 1-isopropyl-10-methyl//acetic acid |
| 67 | $CH_3$ | H | H | H | H | $CH_3$ | n-$C_3H_7$ | $CH_2CO$ | $C_2H_5$ | 3,10-dimethyl-1-propyl//acetic acid |
| 68 | $CH_3$ | H | $C_2H_5$ | $CH_3$ | H | $CH_3$ | $C_2H_5$ | $CH_2CO$ | $C_2H_5$ | 1,4-diethyl-3,10-dimethyl//acetic acid |
| 69 | H | H | H | H | H | $CH_3$ | $CH_3$ | $CH(CH_3)CO$ | $C_2H_5$ | $\alpha$,1,10-trimethyl//acetic acid |
| 70 | H | H | H | H | H | $C_2H_5$ | cyclohexyl | $C(CH_3)_2CO$ | $C_2H_5$ | 1-cyclohexyl-10-ethyl-$\alpha,\alpha$-dimethyl//acetic acid |
| 71 | H | H | H | H | H | $CH_3$ | t-$C_4H_9$ | $CH_2CO$ | $C_2H_5$ | 1-t-butyl-10-methyl//acetic acid |
| 72 | H | H | H | H | H | $CH_3$ | n-$C_4H_9$ | $CH_2CO$ | $C_2H_5$ | 1-butyl-10-methyl//acetic acid |
| 73 | H | H | H | H | 7-$CH_3$ | $C_2H_5$ | n-$C_3H_7$ | $CH_2CO$ | $C_2H_5$ | 10-ethyl-6-methyl-1-propyl//acetic acid |
| 74 | H | H | H | H | 5-Br | $C_2H_5$ | $C_2H_5$ | $CH_2CO$ | $C_2H_5$ | 8-bromo-1,10-diethyl//acetic acid |
| 75 | H | H | H | H | 5-$OCH_3$ | n-$C_4H_9$ | $CH_3$ | $CH_2CO$ | $CH_3$ | 10-butyl-8-methoxy-1-methyl//acetic acid |
| 76 | H | H | H | H | 5-$OCOCH_3$ | t-$C_4H_9$ | $CH_3$ | $CH_2CO$ | $C_2H_5$ | 8-acetoxy-10-t-butyl-1-methyl//acetic acid |

TABLE II-continued

| Ex. | INTERMEDIATE OF FORMULA III IN WHICH $X^1$ IS SH | | | | | KETOESTER OF FORMULA IV, $R^1-\overset{O}{\overset{\|}{C}}-Alk^1-CO-OR^{10}$ | | | PRODUCT: (PREFIX LISTED BELOW)-3,4-DIHYDRO-1H-1,4-THIAZINO-[4,3-a]INDOLE-1-(SUFFIX LISTED BELOW) | |
|---|---|---|---|---|---|---|---|---|---|---|
| | $R^2$ | $R^3$ | $R^4$ | $R^5$ | $R^6$ | $R^7$ | $R^1$ | $Alk^1$-CO | $R^{10}$ | PREFIX//SUFFIX |
| 77 | H | H | H | H | 5-benzyloxy | i-$C_3H_7$ | $CH_3$ | $CH_2CO$ | $C_2H_5$ | 8-benzyloxy-10-isopropyl-1-methyl//acetic acid |
| 78 | H | H | H | H | 4-$CH_3$ | $CH_3$ | n-$C_3H_7$ | $CH_2CO$ | $C_2H_5$ | 9,10-dimethyl-1-propyl//acetic acid |
| 79 | H | H | H | H | 6-$CH_3$ | $CH_3$ | n-$C_3H_7$ | $CH_2CO$ | $C_2H_5$ | 7,10-dimethyl-1-propyl//acetic acid |
| 80 | H | H | H | H | 5-$NO_2$ | n-$C_3H_7$ | n-$C_3H_7$ | $CH_2CO$ | $C_2H_5$ | 8-nitro-1,10-dipropyl//acetic acid |
| 81 | H | H | $CH_3$ | $CH_3$ | H | $CH_3$ | n-$C_3H_7$ | $CH_2CO$ | $C_2H_5$ | 4,4,10-trimethyl-1-propyl//acetic acid |
| 82 | $CH_3$ | $CH_3$ | H | H | 5-$OC_2H_5$ | $C_2H_5$ |  | $CH(C_2H_5)CO$ | $C_2H_5$ | 1-cyclopropyl-α,α,10-triethyl-3,3-dimethyl-8-ethoxy//acetic acid |
| 83 | $CH_3$ | $CH_3$ | $C_2H_5$ | $C_2H_5$ | 6-$C_2H_5$ | n-$C_4H_9$ |  | $C(CH_3)_2CO$ | $C_2H_5$ | 10-butyl-1-cyclohexyl-α,α,3,3-tetramethyl-4,4,7-triethyl//acetic acid |
| 84 | $CH_3$ | H | n-$C_3H_7$ | n-$C_3H_7$ | 4-n-$C_3H_7$ | $CH_3$ | $C_2H_5$ | $CH(CH_3)CO$ | $C_2H_5$ | 1-ethyl-α,3,10-trimethyl-4,4,9-tripropyl//acetic acid |
| 85 | H | H | H | H | H | $C_2H_5$ | n-$C_3H_7$ | $C(CH_3)_2CO$ | $C_2H_5$ | α,α-dimethyl-10-ethyl-propyl//acetic acid |
| 86 | $C_2H_5$ | $C_2H_5$ | $C_2H_5$ | $C_2H_5$ | 4-$C_2H_5$ | $C_2H_5$ | t-$C_4H_9$ | $C(i-C_3H_7)_2CO$ | $C_2H_5$ | 1-t-butyl-α,α-diisopropyl-3,3,4,4,9,10-hexaethyl//acetic acid |
| 87 | H | H | H | H | H | $CH_3$ | $CH_3$ | $CH_2CH_2CO$ | $CH_3$ | 1,10-dimethyl//propionic acid |
| 88 | H | H | H | H | H | $CH_3$ | n-$C_3H_7$ | $CH_2CH_2CO$ | $CH_3$ | 10-methyl-1-propyl//propionic acid |
| 89 | H | H | H | H | 6-OH | $CH_3$ | n-$C_3H_7$ | $CH_2C(C_2H_5)_2CO$ | $C_2H_5$ | β,β-diethyl-7-hydroxy-10-methyl-1-propyl//propionic acid |
| 90 | $CH_3$ | H | H | H | 7-$NO_2$ | $CH_3$ |  | $CH(n-C_3H_7)CH_2CO$ | $C_2H_5$ | 1-cyclobutyl-3,10-dimethyl-6-nitro-α-propyl//propionic acid |
| 91 | H | H | $CH_3$ | H | 5-$CH_3$ | $CH_3$ |  | $C(CH_3)_2C(CH_3)_2CO$ | $C_2H_5$ | 1-cyclopropyl-α,α,β,β,4,8,10-heptamethyl//propionic acid |
| 92 | $CH_3$ | H | H | H | H | $CH_3$ | $CH_3$ | $CH_2C(n-C_3H_7)_2CO$ | $C_2H_5$ | 1,3,10-trimethyl-α,α-dipropyl//propionic acid |
| 93 | $CH_3$ | H | $C_2H_5$ | $C_2H_5$ | H | $CH_3$ | $C_2H_5$ | $CH(CH_3)C(CH_3)_2CO$ | $CH_3$ | α,α,β,3,10-pentamethyl-1,4,4-triethyl//propionic acid |
| 94 | H | H | $CH_3$ | $CH_3$ | H | $C_2H_5$ | $C_2H_5$ | $C(CH_3)_2CH_2CO$ | $CH_3$ | 1,10-diethyl-β,β,4,4-tetramethyl//propionic acid |
| 95 | H | H | n-$C_3H_7$ | H | 4-$O\overset{O}{\overset{\|}{C}}C_2H_5$ | $CH_3$ |  | $C(C_2H_5)_2C(C_2H_5)_2CO$ | $CH_3$ | 1-cyclopentyl-10-methyl-9-propionoxy-4-propyl-α,β,β-triethyl//propionic acid |
| 96 | n-$C_3H_7$ | H | H | H | 4-$OCH_3$ | $CH_3$ | n-$C_3H_7$ | $CH_2CH(CH_3)CO$ | $C_2H_5$ | α,10-dimethyl-1,3-dipropyl-9-methoxy//propionic acid |
| 97 | $C_2H_5$ | H | H | H | 5-$NO_2$ | $CH_3$ | $CH_3$ | $C(C_2H_5)_2C(C_2H_5)_2CO$ | $C_2H_5$ | 1,10-dimethyl-8-nitro-α,α,β,β,3-pentaethyl//propionic acid |
| 98 | $C_2H_5$ | $C_2H_5$ | H | H | 4-$C_2H_5$ | $CH_3$ | n-$C_3H_7$ | $CH(n-C_3H_7)CH_2CO$ | $CH_3$ | β,1-dipropyl-3,3,9,10-tetraethyl//propionic acid |
| 99 | H | H | H | H | 6-$OC_2H_5$ | $C_2H_5$ |  | $CH(C_2H_5)CH(C_2H_5)CO$ | $C_2H_5$ | 1-cyclopropyl-7-ethoxy-α,β,10-triethyl//propionic acid |
| 100 | H | H | H | H | H | $CH_3$ | $CH_3$ | $CH_2CH_2CH_2CO$ | $C_2H_5$ | 1,10-dimethyl//butyric acid |
| 101 | $CH_3$ | H | H | H | H | $CH_3$ | $C_2H_5$ | $CH(CH_3)CH_2CH_2CO$ | $C_2H_5$ | 1-ethyl-γ,3,10-trimethyl//butyric acid |
| 102 | $CH_3$ | $CH_3$ | H | H | H | $CH_3$ | n-$C_3H_7$ | $C(C_2H_5)_2CH_2CH_2CO$ | $C_2H_5$ | γ,γ-diethyl-1-propyl-3,3,10-trimethyl//butyric acid |
| 103 | $C_2H_5$ | H | H | H | 6-$NO_2$ | $C_2H_5$ | n-$C_4H_9$ | $[C(CH_3)_2]_3CO$ | $C_2H_5$ | 1-butyl-3,10-diethyl-7-nitro-α,β,γ-trimethyl//butyric acid |
| 104 | $CH_3$ | $CH_3$ | H | H | 4-n-$C_3H_7$ | n-$C_3H_7$ | n-$C_3H_7$ | $CH_2[CH(C_2H_5)]_2CO$ | $C_2H_5$ | α,β-diethyl-3,3-dimethyl-1,9,10-tripropyl//butyric acid |
| 105 | H | H | H | H | 7-OH | n-$C_4H_9$ | $C_2H_5$ | $C(CH_3)_2CH_2O(CH_3)_2CO$ | $C_2H_5$ | 10-butyl-1-ethyl-6-hydroxy-α,α,γ,γ-tetramethyl//butyric acid |
| 106 | $CH_3$ | H | $CH_3$ | H | 4-$OC_2H_5$ | t-$C_4H_9$ | $C_2H_5$ | $[C(CH_3)_2]_3CO$ | $C_2H_5$ | 10-t-butyl-9-ethoxy-1-ethyl-α,α,β,β,γ,γ,3,4- |

TABLE II-continued

| Ex. | INTERMEDIATE OF FORMULA III IN WHICH $X^1$ IS SH | | | | | | KETOESTER OF FORMULA IV, $R^1-\overset{\overset{O}{\|}}{C}-Alk^1-CO-OR^{10}$ | | | PRODUCT: (PREFIX LISTED BELOW)-3,4-DIHYDRO-1H-1,4-THIAZINO-[4,3-a]INDOLE-1-(SUFFIX LISTED BELOW) |
|---|---|---|---|---|---|---|---|---|---|---|
| | $R^2$ | $R^3$ | $R^4$ | $R^5$ | $R^6$ | $R^7$ | $R^1$ | $Alk^1$-CO | $R^{10}$ | PREFIX//SUFFIX |
| | | | | | | | | | | octomethyl//butyric acid |

EXAMPLE 107

N,1,10-Trimethyl-3,4-dihydro-1H-1,4-oxazino-[4,3-a]indole-1-acetamide (V; $R^1$ and $R^7$ = $CH_3$, $R^2$, $R^3$, $R^4$, $R^5$ and $R^6$ = H, X = O and Z = $CH_2CONHC_2H_5$)

Triethylamine (6 g.) and then ethyl chloroformate (5 g.) are added to a cooled solution (−5° C.) of 1,10-dimethyl-3,4-dihydro-1H-1,4-oxazino[4,3-a]indole-1-acetic acid (10 g.), described in Example 3, in 150 ml. of tetrahydrofuran (THF). After being stirred for 2 hr. at 10° C. the suspension is further cooled to ca. −10° C. and treated with methylamine (66 ml. of the 40% water solution) and stirred at given temperature for an additional hour. Most of the THF is evaporated and the residue partitioned between ether and water. The ether solution is washed with water, dried ($MgSO_4$) and concentrated to afford a solid. The solid is recrystallized from ethyl acetate to afford the title compound, m.p. 131°–133° C.

In the same manner but replacing the 40% aqueous solution of methylamine with an equivalent amount of the amines of formula $HNR^8R^9$, ammonium hydroxide (concentrated), dimethylamine (30% aqueous solution), n-hexylamine (20of aqueous solution), diethylamine (30% aqueous solution, isopropylamine (40% aqueous solution), ethylamine (70% aqueous solution), pyrrolidine (50% aqueous solution), piperidine, morpholine, N-methylpiperazine, 1,10-dimethyl-3,4-dihydro-1H-1,4-oxazino[4,3-a]indole-1-acetamide, m.p. 156°–157° C., nmr ($CDCl_3$) δ1.69 (3H), 2.33 (3H), N,N,1,10-tetramethyl-3,4-dihydro-1H-1,4-oxazino[4,3-a]indole-1-acetamide, nmr ($CDCl_3$) δ1.78 (3H), 2.33 (3H), 2.95 (6H), 1,10-dimethyl-N-hexyl-3,4-dihydro-1H-1,4-oxazino[4,3-a]indole-1-acetamide, N,N-diethyl-1,10-dimethyl-3,4-dihydro-1H-1,4-oxazino4,3-a]-indole-1-acetamide, 1,10-dimethyl-N-isopropyl-3,4-dihydro-1h-1,4-oxazino[4,3-a]indole-1-acetamide, 1,10-dimethyl-N-ethyl-3,4-dihydro-1H-1,4-oxazino[4,3-a]indole-1-acetamide, m.p. 114°–116° C. 1-[(1,10-dimethyl-3,4-dihydro-1H-1,4-oxazine-[4,3-a]indole-1-yl)acetyl]-pyrrolidine, 1-[(1,10-dimethyl-3,4-dihydro-1H-1,4-oxazino[4,3-a]indol-1-yl)acetyl]piperidine, 4-[(1,10-dimethyl-3,4-dihydro-1H-1,4-oxazino[4,3-a]indol-1-yl)acetyl]morpholine, and 1-methyl-4-[(1,10-dimethyl-3,4-dihydro-1H-1,4-oxazino[4,3-a]indol-1-yl)acetyl]piperazine, are obtained respectively.

By following the procedure of Example 107 but using as starting material an equivalent amount of one of the acid compounds of formula V, described in Examples 14 to 106, instead of 3,4-dihydro-1,10-dimethyl-3,4-dihydro-1H-1,4-oxazino[4,3-a]indole-1-acetic acid, and using an equivalent amount of an appropriate amine such as ammonia or a primary or secondary amine described in Example 107, then the corresponding amide compound of formula V is obtained. Examples of such amides are listed as products in Tables III, IV, V and VI together with the appropriate starting material and amine used for the preparation of the amide. In each case the starting material is noted by the example in which it is prepared.

TABLE III

| EXAMPLE | NO. OF THE EXAMPLE IN WHICH STARTING MATERIAL IS PREPARED | AMINE | PRODUCT: [(PREFIX LISTED BELOW)-3,4-DIHYDRO-1H-1,4-OXAZINO[4,3-a]-INDOLE-1-(SUFFIX LISTED BELOW] PREFIX//SUFFIX |
|---|---|---|---|
| 108 | 4 | $CH_3NH_2$ | N,1,10-trimethyl//propionamide, m.p. 147 – 149° C. |
| 109 | 4 | $NH_3$ | 1,10-dimethyl//propionamide, m.p. 97 – 98° C. |
| 110 | 4 | $(CH_3)_2NH$ | N,N,1,10-tetramethyl//propionamide, nmr ($CDCl_3$) δ1.64 (3H), 2.33 (3H), 2.88 (6H) |
| 111 | 4 | $C_2H_5NH_2$ | 1,10-dimethyl-N-ethyl//propionamide, m.p. 104 – 106° C. |
| 112 | 4 | $(C_2H_5)_2NH$ | N,N-diethyl-1,10-dimethyl//propionamide |
| 113 | 5 | $CH_3NH_2$ | N,1,10-trimethyl//carboxamide |
| 114 | 5 | $NH_3$ | 1,10-dimethyl//carboxamide |
| 115 | 6 | $(CH_3)_2NH$ | 1-ethyl-N,N,3,10-tetramethyl//carboxamide |
| 116 | 7 | n-$C_6H_{13}NH_2$ | 1,3-diisopropyl-8,10-dimethyl-N-hexyl//carboxamide |
| 117 | 8 | $C_2H_5NH_2$ | N-ethyl-8-hydroxy-1,3,3,10-tetramethyl//carboxamide |
| 118 | 9 | $CH_3NH_2$ | 6,10-diethyl-N-methyl-1-propyl//carboxamide |
| 119 | 10 | $(CH_3)_2NH$ | 1-cyclopropyl-N,N-dimethyl-4,10-isopropyl//carboxamide |
| 120 | 11 | $(CH_3)_2NH$ | 1-cyclopentyl-4,4,10-triethyl-N,N,3,3-tetramethyl//carboxamide |
| 121 | 12 | $CH_3NH_2$ | N,1,4,10-tetramethyl//acetamide |

TABLE III-continued

| EXAMPLE | NO. OF THE EXAMPLE IN WHICH STARTING MATERIAL IS PREPARED | AMINE | PRODUCT: [(PREFIX LISTED BELOW)-3,4-DIHYDRO-1H-1,4-OXAZINO[4,3-a]-INDOLE-1-(SUFFIX LISTED BELOW] PREFIX//SUFFIX |
|---|---|---|---|
| 122 | 13 | $NH_3$ | 1-ethyl-10-methyl//acetamide |
| 123 | 13 | $(CH_3)_2NH$ | 1-ethyl-N,N,10-trimethyl//acetamide |
| 124 | 13 | $n-C_6H_{13}NH_2$ | 1-ethyl-N-hexyl-10-methyl//acetamide |
| 125 | 13 | $(C_2H_5)_2NH$ | 10-methyl-N,N,1-triethyl//acetamide |
| 126 | 14 | $CH_3NH_2$ | N,10-dimethyl-1-propyl//acetamide, m.p. 96 – 98° C. |
| 127 | 14 | $NH_3$ | 10-methyl-1-propyl//acetamide |
| 128 | 14 | $(CH_3)_2NH$ | 1-propyl-N,N,10-trimethyl//acetamide, m.p. 84 – 86° C. |
| 129 | 14 | $n-C_6H_{13}NH_2$ | N-hexyl-10-methyl-1-propyl//acetamide |
| 130 | 14 | $(C_2H_5)_2NH$ | N,N-diethyl-10-methyl-1-propyl//acetamide |
| 131 | 15 | $CH_3NH_2$ | N,10-dimethyl-1-isopropyl//acetamide |
| 132 | 15 | $(C_2H_5)_2NH$ | N,N-diethyl-1-isopropyl-10-methyl//acetamide |
| 133 | 16 | $CH_3NH_2$ | 1-propyl-N,3,10-trimethyl//acetamide |
| 134 | 16 | $(CH_3)_2NH$ | 1-propyl-N,N,3,10-tetramethyl//acetamide |
| 135 | 17 | $(C_2H_5)_2NH$ | 3,10-dimethyl-N,N,1,4-tetraethyl//acetamide |
| 136 | 18 | $CH_3NH_2$ | N,α,1,10-tetramethyl//acetamide |
| 137 | 18 | $NH_3$ | α,1,10-trimethyl//acetamide |
| 138 | 18 | $(CH_3)_2NH$ | N,N,α,1,10-pentamethyl//acetamide |
| 139 | 19 | $C_2H_5NH_2$ | 1-cyclohexyl-N,10-diethyl-α,α-dimethyl//acetamide |
| 140 | 20 | $CH_3NH_2$ | 1-t-butyl-N,10-dimethyl//acetamide |
| 141 | 21 | $CH_3NH_2$ | 1-butyl-N,10-dimethyl//acetamide |
| 142 | 22 | $C_2H_5NH_2$ | N,10-diethyl-6-methyl-1-propyl//acetamide |
| 143 | 23 | $(C_2H_5)_2NH$ | 8-bromo-N,N,1,10-tetraethyl//acetamide |
| 144 | 24 | $NH_3$ | 10-butyl-8-methoxy-1-methyl//acetamide |
| 145 | 25 | $t-C_4H_9NH_2$ | 8-acetoxy-N,10-di-t-butyl-1-methyl//acetamide |
| 146 | 26 | $NH_3$ | 8-benzyloxy-10-isopropyl-1-methyl//acetamide |
| 147 | 27 | $(CH_3)_2NH$ | 1-propyl-N,N,9,10-tetramethyl//acetamide |
| 148 | 28 | $(C_2H_5)_2NH$ | N,N-diethyl-7,10-dimethyl-1-propyl//acetamide |
| 149 | 29 | $n-C_6H_{13}NH_2$ | 1,10-dipropyl-N-hexyl-8-nitro//acetamide |
| 150 | 30 | $CH_3NH_2$ | 1-propyl-N,4,4,10-tetramethyl//acetamide |
| 151 | 31 | $NH_3$ | 1-cyclopropyl-α,α,10-triethyl-3,3-dimethyl-8-ethoxy//acetamide |
| 152 | 32 | $C_2H_5NH_2$ | 10-butyl-1-cyclohexyl-α,α,3,3-tetramethyl-N,4,4,7-tetraethyl//acetamide |
| 153 | 33 | $CH_3NH_2$ | 1-ethyl-N,α,3,10-tetramethyl-4,4,9-tripropyl//acetamide |
| 154 | 34 | $(CH_3)_2NH$ | 10-ethyl-1-propyl-N,N,α,α-tetramethyl//acetamide |
| 155 | 35 | $(C_2H_5)_2NH$ | 1-t-butyl-α,α-diisopropyl-N,N,3,3-4,4,9,10-octaethyl//acetamide |
| 156 | 36 | $CH_3NH_2$ | N,10-dimethyl-9-iodo-1-isopropyl//propionamide |
| 157 | 38 | $CH_3NH_2$ | β,β-diethyl-N,10-dimethyl-7-hydroxy-1-propyl//propionamide |
| 158 | 39 | $NH_3$ | 1-cyclobutyl-3,10-dimethyl-6-nitro-α-propyl//propionamide |
| 159 | 43 | $C_2H_5NH_2$ | β,β,4,4-tetramethyl-N,1,10-triethyl//propionamide |
| 160 | 45 | $n-C_3H_7NH_2$ | α,10-dimethyl-9-methoxy-N,1,3-tripropyl//propionamide |
| 161 | 48 | $C_2H_5NH_2$ | 1-cyclopropyl-7-ethoxy-N,α,β10-triethyl//propionamide |
| 162 | 49 | $CH_3NH_2$ | N,1,10-trimethyl//butyramide |
| 163 | 49 | $(CH_3)_2NH$ | N,N,1,10-tetramethyl//butyramide |
| 164 | 52 | $n-C_4H_9NH_2$ | N,1-dibutyl-3,10-diethyl-7-nitro-α,β,γ-trimethyl//butyramide |
| 165 | 53 | $(n-C_3H_7)_2NH$ | α,β-diethyl-3,3-dimethyl-N,N,1,9,10-pentapropyl//butyramide |
| 166 | 54 | $n-C_4H_9NH_2$ | N,10-dibutyl-1-ethyl-6-hydroxy-α,α,γ,γ-tetramethyl//butyramide |
| 167 | 55 | $(t-C_4H_9)_2NH$ | 9-ethoxy-1-ethyl-α,α,β,β,γ,γ,3,4-octomethyl-N,N,10-tri-t-butyl//butyramide |

TABLE IV

| EXAMPLE | NO. OF THE EXAMPLE IN WHICH STARTING MATERIAL IS PREPARED | AMINE | PRODUCT: [(PREFIX LISTED BELOW)-3,4-DIHYDRO-1H-1,4-OXAZINO[4,3-a]-INDOLE-1-(SUFFIX LISTED BELOW)] PREFIX//SUFFIX |
|---|---|---|---|
| 168 | 4 | pyrrolidine | 1-[(1,10-dimethyl//propionyl]-pyrrolidine |
| 169 | 4 | piperidino | 1-[(1,10-dimethyl//propionyl]-piperidine |
| 170 | 4 | morpholine | 4-[(1,10-dimethyl//propionyl]-morpholine, m.p. 160 – 162° C. |
| 171 | 4 | piperazine | 1-[(1,10-dimethyl//propionyl]-piperazine |
| 172 | 4 | N-methyl-piperazine | 1-methyl-4-[(1,10-dimethyl//propionyl]piperazine |
| 173 | 4 | N-piperazine-ethanol | 1-(2-hydroxyethyl)-4-[(1,10-dimethyl//propionyl]piperazine |
| 174 | 5 | pyrrolidine | 1-[(1,10-dimethyl//carbonyl]-pyrrolidine |
| 175 | 5 | morpholine | 4-[(1,10-dimethyl//carbonyl]-morpholine |
| 176 | 6 | N-ethyl-piperazine | 1-ethyl-4-[(1-ethyl-3,10-dimethyl//carbonyl]piperazine |
| 177 | 12 | piperidine | 1-[(1,4,10-trimethyl//acetyl]-piperidine |
| 178 | 13 | morpholine | 4-[(1-ethyl-10-methyl//acetyl]-morpholine |
| 179 | 13 | N-piperazine-propanol | 1-(3-hydroxypropyl)-4-[(1-ethyl-10-methyl//acetyl]piperazine |
| 180 | 14 | pyrrolidine | 1-[(10-methyl-1-propyl//acetyl]-pyrrolidine |
| 181 | 14 | morpholine | 4-[(10-methyl-1-propyl//acetyl]-morpholine |
| 182 | 15 | piperidine | 1-[(1-isopropyl-10-methyl//acetyl]piperidine |
| 183 | 16 | piperazine | 1-[(3,10-dimethyl-1-propyl//acetyl]piperazine |
| 184 | 18 | N-ethyl-piperazine | 1-ethyl-4-[(α,1,10-trimethyl//acetyl]piperazine |
| 185 | 26 | pyrrolidine | 1-[(8-benzyloxy-10-isopropyl-1-methyl//acetyl]pyrrolidine |
| 186 | 27 | piperidine | 1-[(9,10-dimethyl-1-propyl//acetyl]piperidine |
| 187 | 31 | morpholine | 4-[(1-cyclopropyl-α,α,10-triethyl-3,3-dimethyl-8-ethoxy//acetyl]-morpholine |
| 188 | 37 | piperazine | 1-[6-acetoxy-1,10-diethyl-α,3,3,-4,4-pentamethyl//propionyl]-piperazine |
| 189 | 40 | N-piperazine-ethanol | 1-(2-hydroxyethyl)-4-[(1-cyclo-propyl-α,α,β,β,4,8,10-heptamethyl//propionyl]piperazine |
| 190 | 41 | pyrrolidine | 1-[(1,3,10-trimethyl-α,α-dipropyl//propionyl]pyrrolidine |
| 191 | 43 | morpholine | 4-[(1,10-diethyl-β,β,4,4-tetramethyl//propionyl]morpholine |
| 192 | 48 | N-propyl-piperazine | 1-propyl-4-[(1-cyclopropyl-7-ethoxy-α,β,10-triethyl//propionyl]piperazine |
| 193 | 49 | pyrrolidine | 1-[(1,10-dimethyl//butyryl]-pyrrolidine |
| 194 | 49 | N-piperazine-methanol | 1-(hydroxymethyl)-4-[(1,10-dimethyl//butyryl]piperazine |
| 195 | 51 | piperidine | 1-[γ,γ-diethyl-1-propyl-3,3,10-trimethyl//butyryl]piperidine |

TABLE V

| EXAMPLE | NO. OF THE EXAMPLE IN WHICH STARTING MATERIAL IS PREPARED | AMINE | PRODUCT: [PREFIX LISTED BELOW)-3,4-DIHYDRO-1H-1,4-THIAZINO[4,3-a]-INDOLE-1-(SUFFIX LISTED BELOW)] PREFIX//SUFFIX |
|---|---|---|---|
| 196 | 87 | $CH_3NH_2$ | N,1,10-trimethyl//propionamide, |
| 197 | 87 | $NH_3$ | 1,10-dimethyl//propionamide |
| 198 | 87 | $(CH_3)_2NH$ | N,N,1,10-tetramethyl//propionamide |
| 199 | 87 | $C_2H_5NH_2$ | 1,10-dimethyl-N-ethyl//propionamide |
| 200 | 87 | $(C_2H_5)_2NH$ | N,N-diethyl-1,10-dimethyl//propionamide |
| 201 | 56 | $CH_3NH_2$ | N,1,10-trimethyl//carboxamide |
| 202 | 56 | $NH_3$ | 1,10-dimethyl//carboxamide |
| 203 | 57 | $(CH_3)_2NH$ | 1-ethyl-N,N,3,10-tetramethyl//carboxamide |
| 204 | 58 | $n\text{-}C_6H_{13}NH_2$ | 1,3-diisopropyl-8,10-dimethyl-N-hexyl//carboxamide |
| 205 | 59 | $C_2H_5NH_2$ | N-ethyl-8-hydroxy-1,3,3,10-tetramethyl//carboxamide |
| 206 | 60 | $CH_3NH_2$ | 6,10-diethyl-N-methyl-1-propyl//carboxamide |
| 207 | 61 | $(CH_3)_2NH$ | 1-cyclopropyl-N,N-dimethyl-4,10-isopropyl//carboxamide |

TABLE V-continued

| EXAMPLE | NO. OF THE EXAMPLE IN WHICH STARTING MATERIAL IS PREPARED | AMINE | PRODUCT: [PREFIX LISTED BELOW)-3,4-DIHYDRO-1H-1,4-THIAZINO[4,3-a]-INDOLE-1-(SUFFIX LISTED BELOW)] PREFIX//SUFFIX |
|---|---|---|---|
| 208 | 62 | $(CH_3)_2NH$ | 1-cyclopentyl-4,4,10-triethyl-N,N,3,3-tetramethyl//carboxamide |
| 209 | 63 | $CH_3NH_2$ | N,1,10-trimethyl//acetamide |
| 210 | 64 | $NH_3$ | 1-ethyl-10-methyl//acetamide |
| 211 | 64 | $(CH_3)_2NH$ | 1-ethyl-N,N,10-trimethyl//acetamide |
| 212 | 64 | $n-C_6H_{13}NH_2$ | 1-ethyl-N-hexyl-10-methyl//acetamide |
| 213 | 64 | $(C_2H_5)_2NH$ | 10-methyl-N,N,1-triethyl//acetamide |
| 214 | 65 | $CH_3NH_2$ | N,10-dimethyl-1-propyl//acetamide |
| 215 | 65 | $NH_3$ | 10-methyl-1-propyl//acetamide |
| 216 | 65 | $(CH_3)_2NH$ | 1-propyl-N,N,10-trimethyl//acetamide |
| 217 | 65 | $n-C_6H_{13}NH_2$ | N-hexyl-10-methyl-1-propyl//acetamide |
| 218 | 65 | $(C_2H_5)_2NH$ | N,N-diethyl-10-methyl-1-propyl//acetamide |
| 219 | 66 | $CH_3NH_2$ | N,10-dimethyl-1-isopropyl//acetamide |
| 220 | 66 | $(C_2H_5)_2NH$ | N,N-diethyl-1-isopropyl-10-methyl//acetamide |
| 221 | 67 | $CH_3NH_2$ | 1-propyl-N,3,10-trimethyl//acetamide |
| 222 | 67 | $(CH_3)_2NH$ | 1-propyl-N,N,3,10-tetramethyl//acetamide |
| 223 | 68 | $(C_2H_5)_2NH$ | 3,10-dimethyl-N,N,1,4-tetraethyl//acetamide |
| 224 | 69 | $CH_3NH_2$ | N,α,1,10-tetramethyl//acetamide |
| 225 | 69 | $NH_3$ | α,1,10-trimethyl//acetamide |
| 226 | 69 | $(CH_3)_2NH$ | N,N,α,1,10-pentamethyl//acetamide |
| 227 | 70 | $C_2H_5NH_2$ | 1-cyclohexyl-N,10-diethyl-α,α-dimethyl//acetamide |
| 228 | 71 | $CH_3NH_2$ | 1-t-butyl-N,10-dimethyl//acetamide |
| 229 | 72 | $CH_3NH_2$ | 1-butyl-N,10-dimethyl//acetamide |
| 230 | 73 | $C_2H_5NH_2$ | N,10-diethyl-6-methyl-1-propyl//acetamide |
| 231 | 74 | $(C_2H_5)_2NH$ | 8-bromo-N,N,1,10-tetraethyl//acetamide |
| 232 | 75 | $NH_3$ | 10-butyl-8-methoxy-1-methyl//acetamide |
| 233 | 76 | $t-C_4H_9NH_2$ | 8-acetoxy-N,10-di-t-butyl-1-methyl//acetamide |
| 234 | 77 | $NH_3$ | 8-benzyloxy-10-isopropyl-1-methyl//acetamide |
| 235 | 78 | $(CH_3)_2NH$ | 1-propyl-N,N,9,10-tetramethyl//acetamide |
| 236 | 79 | $(C_2H_5)_2NH$ | N,N-diethyl-7,10-dimethyl-1-propyl//acetamide |
| 237 | 80 | $n-C_6H_{13}NH_2$ | 1,10-dipropyl-N-hexyl-8-nitro//acetamide |
| 238 | 81 | $CH_3NH_2$ | 1-propyl-N,4,4,10-tetramethyl//acetamide |
| 239 | 82 | $NH_3$ | 1-cyclopropyl-α,α,10-triethyl-3,3-dimethyl-8-ethoxy//acetamide |
| 240 | 83 | $C_2H_5NH_2$ | 10-butyl-1-cyclohexyl-α,α,3,3-tetramethyl-N,4,4,7-tetraethyl//acetamide |
| 241 | 84 | $CH_3NH_2$ | 1-ethyl-N,α,3,10-tetramethyl-4,4,9-tripropyl//acetamide |
| 242 | 85 | $(CH_3)_2NH$ | 10-ethyl-1-propyl-N,N,α,α-tetramethyl//acetamide |
| 243 | 86 | $(C_2H_5)_2NH$ | 1-t-butyl-α,α-diisopropyl-N,N,3,3,4,4,9,10-octaethyl//acetamide |
| 244 | 88 | $CH_3NH_2$ | N,10-dimethyl-1-propyl//propionamide |
| 245 | 88 | $(CH_3)_2NH$ | 1-propyl-N,N,10-trimethyl//propionamide |
| 246 | 90 | $NH_3$ | 1-cyclobutyl-3,10-dimethyl-6-nitro-α-propyl//propionamide |
| 247 | 94 | $C_2H_5NH_2$ | β,β,4,4-tetramethyl-N,1,10-triethyl//propionamide |
| 248 | 96 | $n-C_3H_7NH_2$ | α,10-dimethyl-9-methoxy-N,1,3-tripropyl//propionamide |
| 249 | 99 | $C_2H_5NH_2$ | 1-cyclopropyl-7-ethoxy-N,α,β,10-triethyl//propionamide |
| 250 | 100 | $CH_3NH_2$ | N,1,10-trimethyl//butyramide |
| 251 | 100 | $(CH_3)_2NH$ | N,N,1,10-tetramethyl//butyramide |
| 252 | 103 | $n-C_4H_9NH_2$ | N,1-dibutyl-3,10-diethyl-7-nitro-α,β,γ-trimethyl//butyramide |
| 253 | 104 | $(n-C_3H_7)_2NH$ | α,β-diethyl-3,3-dimethyl-N,N,1,9,10-pentapropyl//butyramide |
| 254 | 105 | $n-C_4H_9NH_2$ | N,10-dibutyl-1-ethyl-6-hydroxy-α,α,γ,γ-tetramethyl//butyramide |
| 255 | 106 | $(t-C_4H_9)_2NH$ | 9-ethoxy-1-ethyl-α,α,β,β,γ,γ,3,4-octamethyl-N,N,10-tri-t-butyl//butyramide |

TABLE VI

| EXAMPLE | NO. OF THE EXAMPLE IN WHICH STARTING MATERIAL IS PREPARED | AMINE | PRODUCT: [(PREFIX LISTED BELOW)-3,4-DIHYDRO-1H-1,4-THIAZINO[4,3-a]INDOLE-1-(SUFFIX LISTED BELOW)] PREFIX//SUFFIX |
|---|---|---|---|
| 256 | 87 | pyrrolidine | 1-[(1,10-dimethyl//propionyl]-pyrrolidine |
| 257 | 87 | piperidine | 1-[1,10-dimethyl//propionyl]-piperidine |
| 258 | 87 | morpholine | 4-[(1,10-dimethyl//propionyl]-morpholine |
| 259 | 87 | piperazine | 1-[(1,10-dimethyl//propionyl]-piperazine |
| 260 | 87 | N-methyl-piperazine | 1-methyl-4-[(1,10-dimethyl//propionyl]piperazine |
| 261 | 87 | N-piperazine-ethanol | 1-(2-hydroxyethyl)-4-[(1,10-dimethyl//propionyl]piperazine |
| 262 | 56 | pyrrolidine | 1-[(1,10-dimethyl//carbonyl]-pyrrolidine |
| 263 | 56 | morpholine | 4-[(1,10-dimethyl//carbonyl]-morpholine |
| 264 | 57 | N-ethyl-piperazine | 1-ethyl-4-[(1-ethyl-3,10-dimethyl//carbonyl]piperazine |
| 265 | 63 | piperidine | 1-[(1,4,10-trimethyl//acetyl]-piperidine |
| 266 | 64 | morpholine | 4-[(1-ethyl-10-methyl//acetyl]-morpholine |
| 267 | 64 | N-piperazine-propanol | 1-(3-hydroxypropyl)-4-[(1-ethyl-10-methyl//acetyl]piperazine |
| 268 | 65 | pyrrolidine | 1-[(10-methyl-1-propyl//acetyl]-pyrrolidine |
| 269 | 65 | morpholine | 4-[(10-methyl-1-propyl//acetyl]-morpholine |
| 270 | 65 | piperidine | 1-[(1-isopropyl-10-methyl//acetyl]piperidine |
| 271 | 67 | piperazine | 1-[(3,10-dimethyl-1-propyl//acetyl]piperazine |
| 272 | 69 | N-ethyl-piperazine | 1-ethyl-4-[(α,1,10-trimethyl//acetyl]piperazine |
| 273 | 77 | pyrrolidine | 1-[(8-benzyloxy-10-isopropyl-1-methyl//acetyl]pyrrolidine |
| 274 | 78 | piperidine | 1-[(9,10-dimethyl-1-propyl//acetyl]piperidine |
| 275 | 82 | morpholine | 4-[(1-cyclopropyl-α,α-10-triethyl-3,3-dimethyl-8-ethoxy//acetyl]-morpholine |
| 276 | 88 | piperazine | 1-[(10-methyl-1-propyl//propionyl]piperidine |
| 277 | 91 | N-piperazine-ethanol | 1-(2-hydroxyethyl)-4-[(1-cyclopropyl-α,α,β,β,4,8,10-heptamethyl//propionyl]piperazine |
| 278 | 92 | pyrrolidine | 1-[(1,3,10-trimethyl-α,α-dipropyl//propionyl]pyrrolidine |
| 279 | 94 | morpholine | 4-[(1,10-diethyl-β,β,4,4-tetramethyl//propionyl]morpholine |
| 280 | 99 | N-propyl-piperazine | 1-propyl-4-[(1-cyclopropyl-7-ethoxy-α,β,10-triethyl//propionyl]piperazine |
| 281 | 100 | pyrrolidine | 1-[(1,10-dimethyl//butyryl]-pyrrolidine |
| 282 | 100 | N-piperazine-methanol | 1-(hydroxymethyl)-4-[(1,10-dimethyl//butyryl]piperazine |
| 283 | 102 | piperidine | 1-[γ,γ-diethyl-1-propyl-3,3,10-trimethyl//butyryl]piperidine |

EXAMPLE 284

1,10-Dimethyl-1-[2-(methylamino)ethyl]-3,4-dihydro-1H-1,4-oxazino[4,3-a]indole (I; $R^1$ and $R^7 = CH_3$, $R^2$, $R^3$, $R^4$, $R^5$ and $R^6 = H$ and $AlkNR^8R^9 = CH_2CH_2NHCH_3$)

The amide, N,1,10-trimethyl-3,4-dihydro-1H-1,4-oxazino[4,3-a]indole-1-acetamide (11.0 g.), described in Example 107, in 200 ml. of THF is added dropwise to a stirred mixture of lithium aluminum hydride (6.3 g.) in 200 ml. of THF. The reaction is refluxed for 2 hr. and cooled. The excess hydride destroyed with water. The mixture is filtered and the filtrate evaporated. The residue is taken into ether, washed with water and the solution is evaporated to afford the title compound, nmr (CDCl$_3$) δ1.62 (s, 3H), 2.34 (s, 3H).

The corresponding hydrobromic acid addition salt, 1,10-dimethyl-1-[2-(methylamino)ethyl]-3,4-dihydro-1H-1,4-oxazino[4,3-a]indole hydrobromide, has m.p. 249° – 251° C., after recrystallization from isopropanol.

In the same manner but replacing lithium aluminum hydride with an equivalent amount of lithium aluminum hydride-aluminum chloride, aluminum hydride-aluminum chloride, diborane and sodium borohydride-aluminum chloride, the title compound is also obtained.

In the same manner but replacing N,1,10-trimethyl-3,4-dihydro-1H-1,4-oxazino[4,3-a]indole with an equivalent amount of the following amides described in Example 107, 1,10-dimethyl-3,4-dihydro-1H-1,4-oxazino[4,3-a]indole-1-acetamide,
N,N,1,10-tetramethyl-3,4-dihydro-1H-1,4-oxazino[4,3-a]indole-1-acetamide,
1,10-dimethyl-N-hexyl-3,4-dihydro-1H-1,4-oxazino[4,3-a]indole-1-acetamide N,N-diethyl-1,10-dimethyl-3,4-dihydro-1H-1,4-oxazino[4,3-a]indole-1-acetamide,
1,10-dimethyl-N-isopropyl-3,4-dihydro-1H-1,4-oxazino[4,3-a]indole-1-acetamide
1,10-dimethyl-N-ethyl-3,4-dihydro-1H-1,4-oxazino[4,3-a]indole-1-acetamide
1-[(1,10-dimethyl-3,4-dihydro-1H-1,4-oxazino[4,3-a]indole-1-yl)acetyl]pyrrolidine,
1[(1,10-dimethyl-3,4-dihydro-1H-1,4-oxazino[4,3-a]indol-1-yl)acetyl]piperidine,
4-[(1,10-dimethyl-3,4-dihydro-1H-1,4-oxazino[4,3-a]indol-1-yl)acetyl]morpholine, and
1-methyl-4-[(1,10-dimethyl-3,4-dihydro-1H-1,4-oxazino[4,3-a]indol-1-yl)acetyl]piperazine, then there are obtained,
1-(2-aminoethyl)-1,10-dimethyl-3,4-dihydro-1H,1,4-oxazino[4,3-a]indole, nmr (CDCl$_3$) $\delta$1.62 (3H), 2.34 (3H),
1,10-dimethyl-1-[(2-dimethylamino)ethyl]-3,4-dihydro-1H-1,4-oxazino[4,3-a]indole, nmr (CDCl$_3$) $\delta$1.60 (3H), 2.30 (3H), corresponding hydrochloric acid addition salt (hyrochloride) has m.p. 237°–239° C., after recrystallization from methanol-ether,
1,10-dimethyl-1-[2-(hexylamino)ethyl]-3,4-dihydro-1H-1,4-oxazino[4,3-a]indole,
1-[2-(diethylamino)ethyl]-1,10-dimethyl-3,4-dihydro-1H-1,4-oxazino[4,3-a]indole, nmr (CDCl$_3$) $\delta$1.60 (3H), 2.30 (3H), corresponding hydrobromic acid addition salt (hydrobromide) has m.p. 191° – 193° C., after recrystallization from isopropanol-ether,
1,10-dimethyl-1-[2-(isopropylamino)ethyl]-3,4-dihydro-1H-1,4-oxazino[4,3-a]indole,
1,10-dimethyl-1-[2-(ethylamino)ethyl]-3,4-dihydro-1H-1,4-oxazino[4,3-a]indole, nmr (CDCl$_3$) $\delta$1.58 (3H), 2.32 (3H), corresponding hydrobromic acid addition salt has m.p. 196° 14 198° C., after recrystallization from isopropanol-ether,
1,10-dimethyl-1-[2-(1pyrrolidinyl)ethyl]-3,4-dihydro-1H-1,4-oxazino[4,3-a]indole, nmr (CDCl$_3$) $\delta$1.60 (3H), 2.30 (3H), corresponding hydrochloric acid addition salt has m.p. 223° – 225° C., after recrystallization from isopropanol-ether,
1,10-dimethyl-1-(2-piperidinoethyl)-3,4-dihydro-1H-1,4-oxazino[4,3-a]indole, nmr (CDCl$_3$) $\delta$1.61 (3H), 2.33 (3H), corresponding hydrobromic acid addition salt has m.p. 253° – 255° C., after recrystallization from methanol,
1,10-dimethyl-1-(2-morpholinoethyl)-3,4-dihydro-1H-1,4-oxazino[3,4-a]indole, nmr (CDCl$_3$) $\delta$1.60 (3H), 2.31 (3H), corresponding hydrochloric acid addition salt has m.p. 234° – 236° C., after recrystallization from isopropanol-ether, and
1,10-dimethyl-1-[2-(4-methyl-1-piperazinyl)ethyl]-3,4-dihydro-1H-1,4-oxazino[4,3-a]indole, nmr (CDCl$_3$) $\delta$1.62 (s, 3H), 2.32 (s, 3H) corresponding maleic acid addition salt (dimaleate) has m.p. 196°to – 198° C., after recrystallization from methanol, respectively.

By following the procedure of Example 284 but using as starting material an equivalent amount of one of the amide compounds of formula V, described in Examples 108 to 283 instead of N,1,10-trimethyl-3,4-dihydro-1H-1,4-oxazino[4,3-a]indole-1-acetamide, then the corresponding compounds of formula I are obtained. Examples of such compounds of formula I are listed as products in Tables VII and VIII together with the appropriate starting material. In each case the starting material is noted by the example in which it is prepared.

TABLE VII

| EXAMPLE | NO. OF EXAMPLE IN WHICH STARTING MATERIAL IS PREPARED | PRODUCT: (PREFIX LISTED BELOW)-3,4-DIHYDRO-1H-1,4-OXAZINO[4,3-a]-INDOLE |
| --- | --- | --- |
| 285 | 108 | 1,10-dimethyl-1-[3-(methylamino)propyl], nmr (CDCl$_3$) $\delta$1.62 (3H), 2.32 (3H), corresponding hydrochloric acid addition salt has m.p. 193 – 195° C., after recrystallization from isopropanol-ether |
| 286 | 109 | 1-(3-aminopropyl)-1,10-dimethyl, nmr(CDCl$_3$) $\delta$1.58 (3H), 1.90 (2H), corresponding hydrochloric acid addition salt has m.p. 204 – 206° C., after recrystallization from methanol-ether |
| 287 | 110 | 1,10-dimethyl-1-[3-(dimethylamino)propyl], nmr (CDCl$_3$) $\delta$1.64 (3H), 2.33 (3H), 2.35 (4H), corresponding hydrochloric acid addition salt has m.p. 200 – 201° C., after recrystallization from methanol-ether |
| 288 | 111 | 1,10-dimethyl-1-[3-(ethylamino)propyl], nmr (CDCl$_3$) $\delta$1.61 (3H), 2.33 (3H), corresponding, hydrochloric acid addition salt has m.p. 220 – 220° C., after recrystallization from ethanol-ether |
| 289 | 112 | 1-[3-(diethylamino)propyl]-1,10-dimethyl, nmr (CDCl$_3$) $\delta$0.94 (t, 6H), 1.58 (s, 3H), corresponding hydrobromic acid addition salt has m.p. 174 – 176° C., after recrystallization from isopropanol |
| 290 | 113 | 1,10-dimethyl-1-[(methylamino)methyl] |
| 291 | 114 | 1-(aminomethyl)-1,10-dimethyl |
| 292 | 115 | 1-[(dimethylamino)methyl]-1-ethyl-1,3,10-trimethyl |
| 293 | 116 | 1,3-diisopropyl-8,10-dimethyl-1-[(hexylamino)methyl] |
| 294 | 117 | 1-(ethylamino)methyl-8-hydroxy- |

TABLE VII-continued

| EXAMPLE | NO. OF EXAMPLE IN WHICH STARTING MATERIAL IS PREPARED | PRODUCT: (PREFIX LISTED BELOW)- 3,4-DIHYDRO-1H-1,4-OXAZINO[4,3-a]- INDOLE |
|---|---|---|
| 295 | 118 | 1,3,3,10-tetramethyl 6,10-diethyl-1-(methylamino)methyl-1-propyl |
| 296 | 119 | 1-cyclopropyl-1-(dimethylamino)-methyl-4,10-isopropyl |
| 297 | 120 | 1-cyclopentyl-3,3-dimethyl-1-(dimethylamino)methyl-4,4,10-triethyl |
| 298 | 121 | 1-(methylamino)ethyl-1,4,10-trimethyl |
| 299 | 122 | 1-(2-aminoethyl)-1-ethyl-10-methyl |
| 300 | 123 | 1-[2-(dimethylamino)ethyl]-1-ethyl-10-methyl |
| 301 | 124 | 1-ethyl-1-[2-(hexylamino)ethyl-10-methyl |
| 302 | 125 | 1-[2-(diethylamino)ethyl]-1-ethyl-10-methyl |
| 303 | 126 | 10-methyl-1-[2-(methylamino)ethyl]-1-propyl |
| 304 | 127 | 1-(aminoethyl)-10-methyl-1-propyl |
| 305 | 128 | 1-[2-(dimethylamino)ethyl]-10-methyl-1-propyl, nmr (CDCl₃) 1.64 (3H), 2.34 (3H), corresponding hydrobromic acid addition salt has m.p. 196 – 197° C., after recrystallization iron isopropanol |
| 306 | 129 | 1-[2-(hexylamino)ethyl]-1-methyl-1-propyl |
| 307 | 130 | 1-[2-(diethylamino)ethyl]-1-methyl-1-propyl, nmr (CDCl₃) 1.62 (3H), 2.33 (3H), corresponding hydrobromic acid addition salt has m.p. 165 – 167° C., after recrystallization from isopropanol |
| 308 | 131 | 1-isopropyl-10-methyl-1-[2-(methylamino)ethyl] |
| 309 | 132 | 1-[2-(diethylamino)ethyl-1-isopropyl-10-methyl |
| 310 | 133 | 3,10-dimethyl-1-[2-(methylamino)-ethyl]-1-propyl |
| 311 | 134 | 3,10-dimethyl-1-[2-(dimethylamino)-ethyl]-1-propyl |
| 312 | 135 | 1,4-diethyl-1-[2-(diethylamino)-ethyl]-3,10-dimethyl |
| 313 | 136 | 1,10-dimethyl-1-[1-methyl-2-(methylamino)ethyl] |
| 314 | 137 | 1-(2-amino-1-methylethyl)-1,10-dimethyl |
| 315 | 138 | 1,10-dimethyl-1-[2-(dimethylamino)-1-methylethyl |
| 316 | 139 | 1-cyclohexyl-1-[1,1-dimethyl-2-(ethylamino)ethyl]-10-ethyl |
| 317 | 140 | 1-t-butyl-10-methyl-1-[2-(methylamino)ethyl] |
| 318 | 141 | 1-butyl-10-methyl-1-[2-(methylamino)ethyl] |
| 319 | 142 | 10-ethyl-1-[2-(ethylamino)ethyl]-6-methyl-1-propyl |
| 320 | 143 | 8-bromo-1,10-diethyl-1-[2-(diethylamino)ethyl |
| 321 | 144 | 1-(2-aminoethyl)-10-butyl-8-methoxy-1-methyl |
| 322 | 145 | 8-acetoxy-10-t-butyl-1-[2-(t-butylamino)ethyl]-1-methyl |
| 323 | 146 | 1-(2-aminoethyl)-8-benzyloxy-10-isopropyl-1-methyl |
| 324 | 147 | 9,10-dimethyl-1-[2-(dimethylamino)-ethyl]-1-propyl |
| 325 | 148 | 1-[2-(diethylamino)ethyl]-7,10-dimethyl-1-propyl |
| 326 | 149 | 1,10-dipropyl-1-[2-(hexylamino)-ethyl]-8-nitro |
| 327 | 150 | 1-[2-(methylamino)ethyl]-1-propyl-4,4,10-trimethyl |
| 328 | 151 | 1-cyclopropyl-3,3-dimethyl-1-[2-amino-1,1-dimethyl]-8-ethoxy-10-ethyl |
| 329 | 152 | 10-butyl-1-cyclohexyl-3,3-dimethyl-1-[1,1-dimethyl-2-(ethylamino)-ethyl]-4,4,7-triethyl |
| 330 | 153 | 3,10-dimethyl-1-ethyl-1-[1-methyl-2-(methylamino)ethyl]-4,4,9-tripropyl |
| 331 | 154 | 1-[1,1-dimethyl-2-(dimethylamino)-ethyl]-10-ethyl-1-propyl |
| 332 | 155 | 1-t-butyl-1-[1,1-diisopropyl-2-(diethylamino)ethyl]-3,3,4,4,9,10-hexaethyl |
| 333 | 156 | 9-iodo-1-isopropyl-10-methyl-1-[3-(methylamino)propyl] |
| 334 | 157 | 1-[1,1-diethyl-3-(methylamino)- |

TABLE VII-continued

| EXAMPLE | NO. OF EXAMPLE IN WHICH STARTING MATERIAL IS PREPARED | PRODUCT: (PREFIX LISTED BELOW)- 3,4-DIHYDRO-1H-1,4-OXAZINO[4,3-a]- INDOLE |
|---|---|---|
| | | propyl]-7-hydroxy-10-methyl-1-propyl |
| 335 | 158 | 1-[3-amino-2-propylpropyl]-1-cyclobutyl-3,10-dimethyl-6-nitro |
| 336 | 159 | 1,10-diethyl-4,4-dimethyl-1-[1,1-dimethyl-3-(ethylamino)propyl] |
| 337 | 160 | 1,3-dipropyl-9-methoxy-10-methyl-1-[1-methyl-3-(propylamino)propyl] |
| 338 | 161 | 1-cyclopropyl-7-ethoxy-10-ethyl-1-[2-ethyl-3-(ethylamino)propyl] |
| 339 | 162 | 1,10-dimethyl-1-[4-(methylamino)-butyl |
| 340 | 163 | 1,10-dimethyl-1-[4-(dimethylamino)-butyl |
| 341 | 164 | 1-butyl-1-[4-(butylamino)-1,2,3-trimethylbutyl]-3,10-diethyl-7-nitro |
| 342 | 165 | 1-[1,2-diethyl-4-(dipropylamino)-butyl]-3,3-dimethyl-1,9,10-tripropyl |
| 343 | 166 | 10-butyl-1-[4-(butylamino)-1,1,3,3-tetramethyl-butyl]-1-ethyl-6-hydroxy |
| 344 | 167 | 10-t-butyl-1-[4-(di-t-butylamino)-1,1,2,2,3,3-hexamethylbutyl]-9-ethoxy-1-ethyl |
| 345 | 168 | 1,10-dimethyl-1-[3-(1-pyrrolidinyl)-propyl], nmr (CDCl$_3$) δ1.61 (s, 3H), 4.03 (4H), corresponding hydrobromic acid addition salt has m.p. 154 – 156° C., after recrystallization from isopropanol |
| 346 | 169 | 1,10-dimethyl-1-(3-piperidinopropyl) nmr (CDCl$_3$) δ1.60 (s, 3H), 2.29 (s, 3H), corresponding hydrobromic acid addition salt has m.p. 205 – 207° C., after recrystallization from isopropanol |
| 347 | 170 | 1,10-dimethyl-1-(3-morpholinopropyl) nmr (CDCl$_3$) δ1.60 (s, 3H), 4.02 (4H) corresponding hydrochloric acid addition salt has m.p. 210 – 212° C., after recrystallization from isopropanol |
| 348 | 171 | 1,10-dimethyl-1-(3-piperazinopropyl) |
| 349 | 172 | 1,10-dimethyl-1-[3-(4-methyl-1-piperazinyl)propyl], nmr (CDCl$_3$) δ1.63 (s, 3H), 2.31 (3H) corresponding hydrobomic acid addition salt (dihydrobromide) has m.p. 260 – 262° C. after recrystallization from methanol |
| 350 | 173 | 1-{3-[4-(2-hydroxyethyl)-1-piperazinyl]propyl]}-1,10-dimethyl |
| 351 | 174 | 1,10-dimethyl-1-[(1-pyrrolidinyl)-methyl] |
| 352 | 175 | 1,10-dimethyl-1-(morpholinomethyl) |
| 353 | 176 | 1-ethyl-3,10-dimethyl-1-[(4-methyl-1-piperazinyl)methyl] |
| 354 | 177 | 1,4,10-trimethyl-1-(2-piperidino-ethyl) |
| 355 | 178 | 1-ethyl-10-methyl-1-(2-morpholino-ethyl) |
| 356 | 179 | 1-ethyl-1- 2-[4-(3-hydroxypropyl)-1-piperazinyl]ethyl -10-methyl |
| 357 | 180 | 10-methyl-1-propyl-1-[2-(1-pyrrolidinyl)ethyl] |
| 358 | 181 | 10-methyl-1-propyl-1-(2-morpholino-ethyl) |
| 359 | 182 | 1-isopropyl-10-methyl-1-(2-piperidinoethyl) |
| 360 | 183 | 3,10-dimethyl-1-(2-piperazinoethyl)-1-propyl |
| 361 | 184 | 1-ethyl-10-methyl-1-[1-methyl-2-(4-methyl-1-piperazinyl)ethyl] |
| 362 | 185 | 8-benzyloxy-10-isopropyl-1-methyl-1-[2(1-pyrrolidinyl)ethyl] |
| 363 | 186 | 9,10-dimethyl-1-(2-piperidinoethyl)-1-propyl |
| 364 | 187 | 1-cyclopropyl-1-(1,1-diethyl-2-morpholinoethyl)-3,3-dimethyl-8-ethoxy-10-ethyl |
| 365 | 188 | 6-acetoxy-1,10-diethyl-3,3,4,4-tetramethyl-1-(2-methyl-3-piperazinopropyl) |
| 366 | 189 | 1-cyclopropyl-4,8,10-trimethyl-1-{3-[4-(2-hydroxyethyl)-1-piperazinyl]-1,1,2,2-tetramethylpropyl} |

TABLE VII-continued

| EXAMPLE | NO. OF EXAMPLE IN WHICH STARTING MATERIAL IS PREPARED | PRODUCT: (PREFIX LISTED BELOW)-3,4-DIHYDRO-1H-1,4-OXAZINO[4,3-a]-INDOLE |
|---|---|---|
| 367 | 190 | 1,3,10-trimethyl-1-[2,2-dipropyl-3-(1-pyrrolidinyl)propyl] |
| 368 | 191 | 1,10-diethyl-4,4-dimethyl-1-(1,1-dimethyl-3-morpholinopropyl) |
| 369 | 192 | 1-cyclopropyl-1-[1,2-diethyl-3-(4-propyl-1-piperazinyl)propyl]-7-ethoxy-10-ethyl |
| 370 | 193 | 1,10-dimethyl-1-[4-(1-pyrrolidinyl)-butyl] |
| 371 | 194 | 1,10-dimethyl-1-{4-[4-(hydroxymethyl)-1-piperazinyl]butyl} |
| 372 | 195 | 1-[(1,1-diethyl-4-piperidino)butyl]-1-propyl-3,3,10-trimethyl |

TABLE VIII

| EXAMPLE | NO. OF EXAMPLE IN WHICH STARTING MATERIAL IS PREPARED | PRODUCT: (PREFIX LISTED BELOW)-3,4-DIHYDRO-1H-1,4-THIAZINO[4,3-a]-INDOLE |
|---|---|---|
| 373 | 196 | 1,10-dimethyl-1-[3-(methylamino)-propyl] |
| 374 | 197 | 1-(3-aminopropyl)-1,10-dimethyl |
| 375 | 198 | 1,10-dimethyl-1-[3-(dimethylamino)-propyl] |
| 376 | 199 | 1,10-dimethyl-1-[3-(ethylamino)-propyl] |
| 377 | 200 | 1-[3-(diethylamino)propyl]-1,10-dimethyl |
| 378 | 201 | 1,10-dimethyl-1-[(methylamino)methyl] |
| 379 | 202 | 1-(aminomethyl)-1,10-dimethyl |
| 380 | 203 | 1-[(dimethylamino)methyl]-1-ethyl-1,3,10-trimethyl |
| 381 | 204 | 1,3-diisopropyl-8,10-dimethyl-1-[(hexylamino)methyl] |
| 382 | 205 | 1-(ethylamino)methyl-8-hydroxy-1,3,3,10-tetramethyl |
| 383 | 206 | 6,10-diethyl-1-(methylamino)methyl-1-propyl |
| 384 | 207 | 1-cyclopropyl-1-(dimethylamino)-methyl-4,10-isopropyl |
| 385 | 208 | 1-cyclopentyl-3,3-dimethyl-1-(dimethylamino)methyl-4,4,10-triethyl |
| 386 | 209 | 1-(methylamino)ethyl-1,4,10-tri-methyl |
| 387 | 210 | 1-(2-aminoethyl)-1-ethyl-10-methyl |
| 388 | 211 | 1-[2-(dimethylamino)ethyl]-1-ethyl-10-methyl |
| 389 | 212 | 1-ethyl-1-[2-(hexylamino)ethyl]-10-methyl |
| 390 | 213 | 1-[2-(diethylamino)ethyl]-1-ethyl-10-methyl |
| 391 | 214 | 10-methyl-1-[2-(methylamino)ethyl]-1-propyl |
| 392 | 215 | 1-(aminoethyl)-10-methyl-1-propyl |
| 393 | 216 | 1-[2-(dimethylamino)ethyl]-10-methyl-1-propyl |
| 394 | 217 | 1-[2-(hexylamino)ethyl]-1-methyl-1-propyl |
| 395 | 218 | 1-[2-(diethylamino)ethyl]-1-methyl-1-propyl |
| 396 | 219 | 1-isopropyl-10-methyl-1-[2-(methyl-amino)ethyl] |
| 397 | 220 | 1-[2-(diethylamino)ethyl-1-isopropyl-10-methyl |
| 398 | 221 | 3,10-dimethyl-1-[2-(methylamino)-ethyl]-1-propyl |
| 399 | 222 | 3,10-dimethyl-1-[2-(dimethylamino)-ethyl]-1-propyl |
| 400 | 223 | 1,4-diethyl-1-[2-(diethylamino)ethyl]-3,10-dimethyl |
| 401 | 224 | 1,10-dimethyl-1-[1-methyl-2-(methyl-amino)ethyl] |
| 402 | 225 | 1-(2-amino-1-methylethyl)-1,10-dimethyl |
| 403 | 226 | 1,10-dimethyl-1-[2-(dimethylamino)-1-methylethyl |
| 404 | 227 | 1-cyclohexyl-1-[1,1-dimethyl-2-(ethylamino)ethyl]-10-ethyl |
| 405 | 228 | 1-t-butyl-10-methyl-1-[2-(methyl-amino)ethyl] |
| 406 | 229 | 1-butyl-10-methyl-1-[2-(methyl-amino)ethyl] |
| 407 | 230 | 10-ethyl-1-[2-(ethylamino)ethyl]-6- |

TABLE VIII-continued

| EXAMPLE | NO. OF EXAMPLE IN WHICH STARTING MATERIAL IS PREPARED | PRODUCT: (PREFIX LISTED BELOW)-3,4-DIHYDRO-1H-1,4-THIAZINO[4,3-a]-INDOLE |
|---|---|---|
| | | methyl-1-propyl |
| 408 | 231 | 8-bromo-1,10-diethyl-1-[2-(diethylamino)ethyl |
| 409 | 232 | 1-(2-aminoethyl)-10-butyl-8-methoxy-1-methyl |
| 410 | 233 | 8-acetoxy-10-t-butyl-1-[2-(t-butylamino)ethyl]-1-methyl |
| 411 | 234 | 1-(2-aminoethyl)-8-benzyloxy-10-isopropyl-1-methyl |
| 412 | 235 | 9,10-dimethyl-1-[2(dimethylamino)ethyl]-1-propyl |
| 413 | 236 | 1-[2-(diethylamino)ethyl]-7,10-dimethyl-1-propyl |
| 414 | 237 | 1,10-dipropyl-1-[2-(hexylamino)ethyl]-8-nitro |
| 415 | 238 | 1-[2-(methylamino)ethyl]-1-propyl-4,4,10-trimethyl |
| 416 | 239 | 1-cyclopropyl-3,3-dimethyl-1-[2-amino-1,1-dimethylethyl[-8-ethoxy-10-ethyl |
| 417 | 240 | 10-butyl-1-cyclohexyl-3,3-dimethyl-1[1,1-dimethyl-2-(ethylamino)ethyl]-4,4,7-triethyl |
| 418 | 241 | 3,10-dimethyl-1-ethyl-1-[1-methyl-2-(methylamino)ethyl]-4,4,9-tripropyl |
| 419 | 242 | 1-[1,1-dimethyl-2-(dimethylamino)ethyl]-10-ethyl-1-propyl |
| 420 | 243 | 1-t-butyl-1-[1,1-diisopropyl-2-(diethylamino)ethyl]-3,3,4,4,9,10-hexaethyl |
| 421 | 244 | 9-iodo-1-isopropyl-10-methyl-1-[3-(methylamino)propyl] |
| 422 | 245 | 1-[1,1-diethyl-3-(ethylamino)propyl]-7-hydroxy-10-methyl-1-propyl |
| 423 | 246 | 1-[3-amino-2-propylpropyl]-1-cyclobutyl-3,10-dimethyl-6-nitro |
| 424 | 247 | 1,10-diethyl-4,4-dimethyl-1-[1,1-dimethyl-3-(ethylamino)propyl |
| 425 | 248 | 1,3-dipropyl-9-methoxy-10-methyl-1-[1-methyl-3-(propylamino)propyl] |
| 426 | 249 | 1-cyclopropyl-7-ethoxy-10-ethyl-1-[2-ethyl-3-(ethylamino)propyl] |
| 427 | 250 | 1,10-dimethyl-1-[4-(methylamino)-butyl |
| 428 | 251 | 1,10-dimethyl-1-[4-(dimethylamino)-butyl |
| 429 | 252 | 1-butyl-1-[4-(butylamino)-1,2,3-trimethylbutyl]3,10-diethyl-7-nitro |
| 430 | 253 | 1-[1,2-dimethyl-4-(dipropylamino)butyl]-3,3-dimethyl-1,9,10-tripropyl |
| 431 | 254 | 10-butyl-1-[4-(butylamino)-1,1,3,3-tetramethylbutyl]-1-ethyl-6-hydroxy |
| 432 | 255 | 10-t-butyl-1-[4-(di-t-butylamino)-1,1,2,2,3,3-hexamethylbutyl]-9-ethoxy-1-ethyl |
| 433 | 256 | 1,10-dimethyl-1-[3-(1-pyrrolidinyl)-propyl |
| 434 | 257 | 1,10-dimethyl-1-(3-piperidinopropyl) |
| 435 | 258 | 1,10-dimethyl-1-(3-morpholinopropyl) |
| 436 | 259 | 1,10-dimethyl-1-(3-piperazinopropyl) |
| 437 | 260 | 1,10-dimethyl-1-[3-(4-methyl-1-piperazinyl)propyl] |
| 438 | 261 | 1-{3-[4-(2-hydroxyethyl)-1-piperazinyl]propyl}-1,10-dimethyl |
| 439 | 262 | 1,10-dimethyl-1-[(1-pyrrolidinyl)-methyl |
| 440 | 263 | 1,10-dimethyl-1-(morpholinomethyl) |
| 441 | 264 | 1-ethyl-3,10-dimethyl-1-[(4-methyl-1-piperazinyl)methyl] |
| 442 | 265 | 1,4,10-trimethyl-1-(2-piperidinoethyl) |
| 443 | 266 | 1-ethyl-10-methyl-1-(2-morpholinoethyl) |
| 444 | 267 | 1-ethyl-1-{2-[4-(3-hydroxypropyl)-1-piperazinyl]ethyl}-10-methyl |
| 445 | 268 | 10-methyl-1-propyl-1-[2-(1-pyrrolidinyl)ethyl] |
| 446 | 269 | 10-methyl-1-propyl-1-(2-morpholinoethyl) |
| 447 | 270 | 1-isopropyl-10-methyl-1-(2-piperidinoethyl) |
| 448 | 271 | 3,10-dimethyl-1-(2-piperazinoethyl)-1-propyl |
| 449 | 272 | 1-ethyl-10-methyl-1-[1-methyl-2-(4-methyl-1-piperazinyl)ethyl] |
| 450 | 273 | 8-benzyloxy-10-isopropyl-1-methyl-1-[2-(1-pyrrolidinyl)ethyl] |
| 451 | 274 | 9,10-dimethyl-1-(2-piperidinoethyl)-1-propyl |

TABLE VIII-continued

| EXAMPLE | NO. OF EXAMPLE IN WHICH STARTING MATERIAL IS PREPARED | PRODUCT: (PREFIX LISTED BELOW)- 3,4-DIHYDRO-1H-1,4-THIAZINO[4,3-a]- INDOLE |
|---|---|---|
| 452 | 275 | 1-cyclopropyl-1-(1,1-diethyl-2-morpholinoethyl)-3,3-dimethyl-8-ethoxy-10-ethyl |
| 453 | 276 | 6-acetoxy-1,10-diethyl-3,3,4,4-tetramethyl-1-(2-methyl-3-piperazinopropyl) |
| 454 | 277 | 1-cyclopropyl-4,8,10-trimethyl-1-{3-[4-(2-hydroxyethyl)-1-piperazinyl]-1,1,2,2-tetramethylpropyl} |
| 455 | 278 | 1,3,10-trimethyl-1-[2,2-dipropyl-3-(1-pyrrolidinyl)propyl] |
| 456 | 279 | 1,10-diethyl-4,4-dimethyl-1-(1,1-dimethyl-3-morpholinopropyl) |
| 457 | 280 | 1-cyclopropyl-1-[1,2-diethyl-3-(4-propyl-1-piperazinyl)propyl]-7-ethoxy-10-ethyl |
| 458 | 281 | 1,10-dimethyl-1-[4-(1-pyrrolidinyl)butyl] |
| 459 | 282 | 1,10-dimethyl-1-{4-[4-(hydroxymethyl)-1-piperazinyl]butyl} |
| 460 | 283 | 1-[(1,1-diethyl-piperidino)butyl]-1-propyl-3,3,10-dimethyl |

EXAMPLE 461

N,1,10-Trimethyl-3,4-dihydro-1H-1,4-oxazino[4,3-a]indole-1-carboxamide (V; $R^1$ and $R^7$ = $CH_3$, $R^2$, $R^3$, $R^4$, $R^5$ and $R^6$ = H, X = O and Z = $CONH_2$ By following the procedure of Example 4 (Procedure B) but using an equivalent amount of pyruvamide instead of levulinic acid, the title compound, identical with the product of Example 113, is obtained.

In the same manner but using an equivalent amount of the appropriate starting material of formula III in place of 3-methylindole-1-ethanol together with the appropriate α-, β-, γ-, or δ-ketoamide, the products listed in Tables III and IV may be obtained. For example, by using 3-butyl-5-methoxyindole-1-ethanol and the β-ketoamide, acetoacetamide, in the procedure of this example, 10-butyl-8-methoxy-1-methyl-3,4-dihydro-1H-1,4-oxazino[4,3-a]indole-1-acetamide, identical to the product of Example 144, is obtained.

EXAMPLE 462

1,10-Dimethyl-3,4-dihydro-1H-1,4-oxazino[4,3-a]indole-1-propanol

Procedure A:

The acid intermediate of formula V, 1,10-dimethyl-3,4-dihydro-1H-1,4-oxazino[4,3-a]indole-1-propionic acid (10.4 g.), described in Example 4, in 100 ml. of THF is slowly added to a stirred mixture of lithium aluminum hydride (2 g.) in 100 ml. of THF. The reaction is kept at 0° C. using an ice-water bath. After addition of the acid, the excess of the hydride is destroyed with water and the precipitate is collected on a filter pad. The filtrate is evaporated. The residue is taken into ether and the ether phase is washed with water, dried ($Na_2SO_4$) and evaporated at reduced pressure to afford an oil. Chromatography of the oil on silica gel using 1:1 ethyl acetate-chloroform gives the title compound, $\gamma_{max}^{CHCl_3}$ 3610, 3450, 1080 $cm^{-1}$.

Procedure B:

Alternatively, the title compound is also obtained by following the procedure of Example 4 (Procedure A) but replacing ethyl levulinate with an equivalent amount of the ketoalcohol lower alkyl ester, 5-acetoxypentan-2-one. Note that the procedure of said example includes hydrolysis of the intermediate ester.

EXAMPLE 463

1,10-Dimethyl-1-[3-(methylamino)propyl]-3,4-dihydro-1H-1,4-oxazino[4,3-a]indole (I; $R^1$ and $R^7$ = $CH_3$, $R^2$, $R^3$, $R^4$, $R^5$ and $R^6$ = H, X = O and $AlkNR^8R^9$ = $CH_2CH_2CH_2NECH_3$ 1,10-Dimethyl-3,4-dihydro-1H-1,4-oxazino[4,3-a]indole-1-propanol (9,5 g.), described in Example 462, is dissolved in dry pyridine (20 ml.). p-Toluenesulfonyl chloride (7.4 g.) is added portionwise to the vigorously stirred and cooled solution. The mixture is stirred further at 0° C. for 1 hr,, ice and water is then added and the aqueous mixture is extracted with ether. The combined ether extracts are washed with 10% ice-cold hydrochloric acid, water, 5% sodium bicarbonate water and dried ($Na_2SO_4$). Concentration of the extracts affords 1,10-dimethyl-3,4-dihydro-1H-1,4-oxazino[4,3-a]indole-1-propyl tosylate, $\gamma_{CHCl_3}^{max}$ 1600, 1370, 1190 and 1170 $cm^{-1}$.

The latter tosylate (12.3 g.) is dissolved in dry acetone (100 ml.) and the resulting solution treaded with sodium iodide (15 g.). The mixture is stirred at room temperature for 24 hr. Most of the acetone is removed at reduced pressure, water and ice are added and the resulting brown-colored solution is extracted with ether. The combined ether extracts are washed with 10% sodium thiosulfate solution, water and dried ($Na_2SO_4$). The solvent is evaporated under reduced pressure to give a yellow oil. The oil is subjected to chromatography on silica gel and eluted with benzene. Concentration of the eluate affords 1,10-dimethyl-1-(3-iodopropyl)-3,4-dihydro-1H-1,4-oxazino[4,3-a]indole, nmr ($CDCl_3$) δ1.59 (3H), 3,13 (2H).

A mixture of the latter compound (10.2 g.) in 100 ml. THF and 40% aqueous methylamine (199 ml.) is stirred at room temperature for 6 hr. Most of the tetrahydrofuran is removed at reduced pressure, the milky water solution is extracted with ether and washed with water until the water tests neutral. The extract is dried ($Na_2SO_4$) and evaporated to yield the title compound, identical to the product of Example 285.

By following the procedure of Examples 462 and 463 in sequence but using as starting material in Example 462 an equivalent amount of the appropriate ester intermediate of formula V (in the case of Procedure A) or an appropriate intermediate of formula III, and appropriate ketoalcohol lower alkyl ester of formula IV, described above, (in the case of Procedure B); followed by the use of an appropriate amine of formula $HNR^8R^9$, for example the amines described in Example 107 in the procedure of Example 463, then the respective compounds of formula I, for example those described in Examples 284 to 460, are obtained.

EXAMPLE 464

1-[2-(Diethylamino)ethyl]-10-methyl-1-propyl-3,4-dihydro-1H-1,4-oxazino[4,3-a]indole [I; $R^1$ = $CH_2CH_2CH$. $R^2$, $R^3$, $R^4$, $R^5$ and $R^6$ = H, $R^7$=$CH_3$, X = O and $AlkNR^8R^9$ = $CH_2CH_2N(CH_2CH_3)_2$[

A solution of triethyloxonium fluoroborate (3.5 g., 0.0185 moles) and the amide of formula V, N,N-diethyl-10-methyl-1-propyl-3,4-dihydro-1H-1,4-oxazino[4,3-a]indole-1-acetamide (5.5 g., 0.016 moles), described in Example 130, in 100 ml. of methylene chloride is evaporated at reduced pressure and the residue dissolved in 50 ml. of absolute ethanol. Sodium borohydride (1.35 g., 0.035 moles) is added in portions to the stirred solution at 0° C. When the addition is complete, stirring is continued for 18 hr. at 25° C. The solution is poured into 250 ml. of water and extracted with 3 × 30 ml. portions of ether. The combined extracts are washed with water, dried ($MgSO_4$) and evaporated yielding the title compound, identical to the product of Example 307.

Similarly other amides of formula V, for example those described in Examples 107 to 283, may be reduced to their corresponding oxazinoindoles of formula I.

EXAMPLE 465

1,10-Dimethyl-3,4-dihydro-1H-1,4-oxazino[4,3-a]indole-1-propionaldehyde

N,N-Dicyclohexylcarbodiimide (2.87 g.) is added to a cooled, stirred solution of the primary alcohol, 1,10-dimethyl-3,4-dihydro-1H-1,4-oxazino[4,3-a]indole-1-propanol (1.0 g.), described in Example 462, in 10 ml. of dimethyl sulfoxide-benzene (2:1) containing trifluoroacetic acid (0.18 ml.) and pyridine (0.38 ml.). The reaction is stirred at room temperature under nitrogen for 5 hr. The reaction mixture is now diluted with 100 ml. of ether, followed by the dropwise addition of a solution of oxalic acid (1.26 g.) in 6 ml. of methanol. After thirty minutes, water (100 ml.) is added and the insoluble material is collected. The organic phase is washed with water (2X), 5% aqueous sodium bicarbonate (2X) and water (2X). After drying ($MgSO_4$) the organic phase is evaporated to yield an oil. The oil is purified by chromatography on silica gel. Elution with 10% ether in benzene affords the title compound as an oil, $\gamma_{CHCl_3}^{Max}$ 1720 $cm^{-1}$.

EXAMPLE 466

1,10-Dimethyl-1-[3-(dimethylamino)propyl]-3,4-dihydro1H-1,4-oxazino[4,3-a]indole [I; $R^1$ and $R^7$ = $CH_3$, $R^2$, $R^3$, $R^4$, $R^5$ and $R^6$ = H, X = O and $AlkNR^8R^9$ = $CH_2CH_2CH_2N(CH_3)_2$]

The product of Example 465 is treated with dimethylamine and perchloric acid according to the method of N. J. Leonard and J. V. Paukstelis, J. Org. Chem., 28, 3021 (1963), to yield the corresponding immonium salt. Reduction of the latter compound with sodium borohydride according to the procedure described by E. Schenker, Angew. Chem., 73, 81 (1961), affords the title compound, identical to the product of Example 287.

By following the procedure of Examples 462, 465 and 466 in sequence but using as starting material in Example 462 an equivalent amount of the appropriate acid intermediate of formula V (in the case of Procedure A) or an appropriate intermediate of formula III, and the appropriate ketoalcohol lower alkyl ester of formula IV, described above, (in the case of Procedure B), followed by the use of an appropriate amine of formula $HNR^8R^9$, for example the amines described in Example 107, in the procedure of Example 465, then the respective compounds of formula I, for example those described in Examples 284 to 460, are obtained.

EXAMPLE 467

Oxidation of 1,10-dimethyl-3,4-dihydro-1H-1,4-oxazino[4,3-a]indole-1-propionaldehyde, described in Example 465, with silver oxide according to the method of Delépine and Bonnet, cited above, affords 1,10-dimethyl-3,4-dihydro-1H-1,4-oxazino[4,3-a]indole-1-propionic acid, identical to the product of Example 4.

By following the procedure of Examples 462, 465 and 467, in sequence, but using as starting material in Example 462 an equivalent amount of the appropriate acid intermediate of formula V (in the case of Procedure A) or an appropriate intermediate of formula III and appropriate ketoalcohol lower alkyl ester of formula IV, described above, (in the case of Procedure B); then the respective acid compounds of formula V in which Z is COOH or $Alk^1COOH$ wherein $Alk^1$ is as defined in the first instance, for example the products of Examples 5 to 106, are obtained.

EXAMPLE 468

1-(3-Aminopropyl)-1,10-dimethyl-3,4-dihydro-1H-1,4-oxazino[4,3-a]indole (I; $R^1$ and $R^7$ = $CH_3$, $R^2$, $R^3$, $R^4$, $R^5$ and $R^6$ = H, X = O and $AlkNR^8R^9$ = $CH_2CH_2CH_2NH_2$)

A solution of the aldehyde, 1,10-dimethyl-3,4-dihydro-1H-1,4-oxazino[4,3-a]indole-1-propionaldehyde 1.0 g., described in Example 465, aqueous hydroxylamine hydrochloride (5 ml. of 5N) and aqueous sodium acetate (5.0 ml. of 5N) and methanol (10 ml.) is heated at 50° – 60° C. for 5 min. and then kept at 4° C. for 16 hr. The precipitate is collected and recrystallized from ethanol-water to afford the corresponding oxime of the above aldehyde.

The latter compound (230 mg.) in dry THF (10 ml.) is added dropwise to a stirred mixture of lithium aluminum hydride (200 mg.) in 15 ml. of THF at ice bath temperature. The mixture is stirred for 1 hr., during which time it is allowed to come to room temperature.

Excess lithium aluminum hydride is destroyed by the careful addition of H₂O/THF (1:1). Insoluble material is collected on a filter and the filtrate is concentrated. The concentrate is taken up in ether. The ether solution is dried (MgSO₄), filtered and concentrated to afford the title compound, identical with the product of Example 286.

By following the procedures of Examples 462, 465 and 468, in sequence, but using as starting material in Example 462 an equivalent amount of the appropriate acid intermediate of formula V (in the case of Procedure A) or an appropriate intermediate of formula III together with an appropriate ketoalcohol lower alkyl ester of formula IV, described above, then the respective primary amine of formula I is obtained. More specifically exemplified, by replacing 1,10-dimethyl-3,4-dihydro-1H-1,4-oxazino[4,3-a]indole-1-propionic acid with an equivalent amount of 10-methyl-1-propyl-3,4-dihydro-1H-1,4-oxazino[4,3-a]indole-1-acetic acid, described in Example 14, in the procedure of Example 462 and subjecting the product thereof to the procedures of Examples 465 and 468, then 1-(aminoethyl)-10-methyl-1-propyl-3,4-dihydro-1H-1,4-oxazine[4,3-a]indole, identical to the product of Example 304, is obtained.

EXAMPLE 469

1,10-Dimethyl-1-(3-iodopropyl)-3,4-dihydro-1H-1,4-oxazino[4,3-a]indole (V; $R^1$ and $R^7 = CH_3$, $R^2$, $R^3$, $R^4$, $R^5$ and $R^6 = H$, $X = H$, $X =$ and $Z = CH_2CH_2CH_2I$)

To a solution of 3-methylindole-1-ethanol (15 g.) in 150 ml. of benzene, 5-iodo-2-pentanone (12 g.) is added. The mixture is heated at reflux with 200 mg. of p-toluenesulfonic acid and hydrated alkali-aluminum silicate (Molecular Sieves No. 4). After 1 hour 400 mg. more of acid is added. After a total of 2 hours the reaction is cooled, filtered and washed with 5% sodium bicarbonate, water and dried over sodium sulfate. Evaporation under reduced pressures affords an oil. This oil is purified by chromatography on silica gel. Elution with benzene and concentration of the eluate gives the title compound, identical to the compound of the same name described in Example 463.

By following the procedure of Example 469 but using as starting materials an appropriate intermediate of formula III described above, together with an appropriate β, γ or δ-haloketone of formula IV described above, then the corresponding intermediates of formula V (Z = Alk²—L in which Alk² and L are as described in the first instance) are obtained.

In turn the last said intermediates of formula V may be treated according to conditions described in Example 463 with an appropriate amine of formula HNR⁸R⁹ in which R⁸ and R⁹ are as described in the first instance to yield the corresonding oxazinoindoles of formula I, for instance the products of Examples 284 to 289, and 386 to 438.

EXAMPLE 470

1,10-Dimethyl-1-[3-(ethylamino)propyl]-3,4-dihydro-h-1,4-oxazino-[4,3-a]indole (I: $R^1$ and $R^7 = CH_3$, $R^2$, $R^3$, $R^4$, $R^5$ and $R^6 = H$, $X = O$ and $AlkNR^8R^9 = CH_2CH_2CH_2NHC_2H_5$)

A mixture of 3-methylindole-1-ethanol (4.2 g.) and N-(4-oxopentyl) acetamide (3.7 g), described by L. P. Khun et al., J. Am. Chem. Soc., 89, 3858 (1967), in 300 ml of dry benzene is stirred and heated at reflux. Water is collected in a Dean-Stark trap. After removal of the water five drops of boron trifluoride-etherate is added and the mixture refluxed 30 min. using the water-separator again. After stirring at room temperature overnight the reaction mixture is evaporated to dryness. The solid residue is dissolved in chloroform and washed successively with 10% aqueous sodium bicarbonate, water, and brine. The chloroform solution is dried over magnesium sulfate, filtered, and evaporated to yield 1-[3-(acetamido)propyl]-1,10-dimethyl-3,4-dihydro-1H-1,4-oxazino[4,3-a]indole $\gamma_{max}^{CHCl_3}$ 1650 cm⁻¹.

The latter product (2.6 g) in 80 ml of dry THF is added to a suspension of lithium aluminum hydride in 200 ml of THF. The resultant slurry is stirred and heated at reflux for 2 hours, cooled and 2.4 g of lithium aluminum hydride is added. The mixture is heated at reflux for 16 hours. The mixture is then decomposed with 22.4 ml of water added dropwise over 3 hours while stirring and cooling the mixture. The precipitate is separated by filtration. The filtrate is dried (MgSO₄). Removal of the solvent affords the title compound, identical to the product of Example 288.

By following the procedure of Example 470, but using as starting material an equivalent amount of the appropriate starting material of formula III, for example, those described in Examples 1 to 106 and using an equivalent amount of an appropriate ketoamide of formula

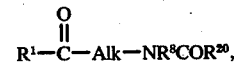

$$R^1-\overset{O}{\underset{\|}{C}}-Alk-NR^8COR^{20},$$

described above, then the respective secondary amine compounds of formula I are obtained.

EXAMPLE 471

1,10-Dimethyl-1-(3-nitropropyl)-3,4-dihydro-1H-1,4-oxazino-[4,3-a]indole (V; $R^1$ and $R^7 = CH_3$, $R^2$, $R^3$, $R^4$, $R^5$ and $R^6 = H$, $X = O$ and $Z = CH_2CH_2NO_2$)

To a solution of 352 mg. of 3-methylindole-1-ethanol and 273 mg. of the nitroketone, 5-nitro-2-pentanone, H. Shechter, et al., cited above, in 100 ml. of benzene is added 5 drops of boron trifluoride etherate and three drops of trifluoroacetic acid. The reaction mixture is stirred and heated at reflux under a water-separator for 18 hr. The benzene solution is cooled, washed with 10% sodium bicarbonate solution, water, saturated brine solution, and dried over magnesium sulfate. The solvent is removed and the residue is subjected to chromatography on silica gel. Elution with chloroform gives the title compound, $\gamma_{max}^{CHCl_3}$ 3450, 1550 cm⁻¹.

Reduction of the latter compound with lithium aluminum hydride according to the procedure of Example 464 affords 1-(3-aminopropyl)-1,10-dimethyl-3,4-dihydro-1H-1,4-oxazino 4,3-a]indole, identical to the product of Example 286.

By following the procedure of Example 471 including the reduction described therein but using as starting material an equivalent amount of the appropriate starting material of formula III, for example, those described in Examples 1 to 100, and using an equivalent amount of an appropriate nitroketone of formula

described above, then the respective primary amine compounds of formula I are obtained.

We claim:

1. A compound of formula

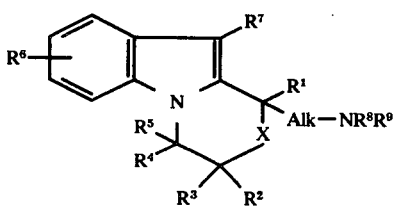

in which $R^1$ is lower alkyl or lower cycloalkyl; $R^2$, $R^3$, $R^4$ and $R^5$ are the same or different selected from the group consisting of hydrogen and lower alkyl; $R^6$ is hydrogen, lower alkyl, hydroxy, lower alkoxy, lower alkanoyloxy, nitro or halo, $R^7$ is lower alkyl; X is oxy; and Alk—$NR^8R^9$ is an amino(lower)alkyl radical in which Alk is an alkylene selected from the group consisting of $CR^{10}R^{11}$, $CR^{10}R^{11}CR^{12}R^{13}$, $CR^{10}R^{11}CR^{12}R^{13}CR^{14}R^{15}$ and $CR^{10}R^{11}CR^{12}R^{13}CR^{14}R^{15}CR^{16}R^{17}$ in which $R^{10}$, $R^{11}$, $R^{12}$, $R^{13}$, $R^{14}$, $R^{15}$, $R^{16}$ and $R^{17}$ are hydrogen or lower alkyl, and $R^8$ and $R^9$ are either the same or different selected from the group consisting of hydrogen and lower alkyl, or $R^8$ and $R^9$ together with the nitrogen atom to which they are joined form a heterocyclic amine radical selected from the group consisting of 1-pyrrolidinyl, piperidino, morpholine, piperazino, 4-(lower alkyl)-1-piperazinyl and 4-[hydroxy(lower)alkyl]-1-piperazinyl.

2. 1,10-Dimethyl-1-[2-(methylamino)ethyl]-3,4-dihydro-1H-1,4-oxazino[4,3-a]indole, as claimed in claim 1.

3. 1-(2-Aminoethyl)-1,10-dimethyl-3,4-dihydro-1H,1,4-oxazino[4,3-a]indole, as claimed in claim 1.

4. 1,10-Dimethyl-1-[(2-dimethylamino)ethyl]-3,4-dihydro-1H-1,4-oxazino[4,3-a]indole, as claimed in claim 1.

5. 1-[2-(Diethylamino)ethyl]-1,10-dimethyl-3,4-dihydro-1H-1,4-oxazino[4,3-a]indole, as claimed in claim 1.

6. 1,10-Dimethyl-1-[2-(ethylamino)ethyl]-3,4-dihydro-1H-1,4-oxazino[4,3-a]indole, as claimed in claim 1.

7. 1,10-Dimethyl-1-[2-pyrrolidinyl)ethyl]-3,4-dihydro-1H-1,4-oxazino[4,3-a]indole, as claimed in claim 1.

8. 1,10-Dimethyl-1-(2-piperidinoethyl)-3,4-dihydro-1H-1,4-oxazino[4,3-a]indole, as claimed in claim 1.

9. 1,10-Dimethyl-1-(2-morpholinoethyl)-3,4-dihydro-1H-1,4-oxazino[4,3-a]indole, as claimed in claim 1.

10. 1,10-Dimethyl-1-[2-(4-methyl-1-piperazinyl)ethyl]-3,4-dihydro-1H-1,4-oxazino[4,3-a]indole, as claimed in claim 1.

11. 1,10-Dimethyl-1-[3-(methylamino)propyl]-3,4-dihydro-1H-1,4-oxazino[4,3-a]indole, as claimed in claim 1.

12. 1-(3-Aminopropyl)-1,10-dimethyl-3,4-dihydro-1H-1,4-oxazino[4,3-a]indole, as claimed in claim 1.

13. 1,10-Dimethyl-1-[3-(dimethylamino)propyl]-3,4-dihydro-1H-1,4-oxazino[4,3-a]indole, as claimed in claim 1.

14. 1,10-Dimethyl-1-[3-(ethylamino)propyl]-3,4dihydro-1H-1,4-oxazino[4,3-a]indole, as claimed in claim 1.

15. 1-[3-Diethylamino)propyl]-1,10-dimethyl-3,4-dihydro-1H-1,4-oxazino[4,3-a]indole, as claimed in claim 1.

16. 1-[2-(Dimethylamino)ethyl]-10-methyl-1-propyl-3,4-dihydro-1H-1,4-oxazino[4,3-a]indole, as claimed in claim 1.

17. 1-[2-(Dimethylamino)ethyl]-10-methyl-1-propyl-3,4-dihydro-1H-1,4-oxazino[4,3-oxazino[4,3-a]indole, as claimed in claim 1.

18. 1,10-Dimethyl-1-[3-pyrrolidinyl)propyl]-3,4-dihydro-1H-1,4-oxazino[4,3-a]indole, as claimed in claim 1.

19. 1,10-Dimethyl-1-(3-piperidiniopropyl)-3,4-dihydro-1H-1,4-oxazino[4,3-a]indole, as claimed in claim 1.

20. 1,10-Dimethyl-1-(3-morpholinopropyl)3,4-dihydro-1H-1,4-oxazino[4,3-a]indole, as claimed in claim 1.

21. 1,10-Dimethyl-1-[3-(4-methyl-1-piperazinyl)propyl]-3,4-dihydro-1H-1,4-oxazino[4,3-a]indole, as claimed in claim 1.

22. A method of treating depression in a mammal which comprises administering to said mammal an antidepressat effective amount from about 0.1 milligram to about 50 milligrams per kilogram of mammal weight per day of a compound of formula

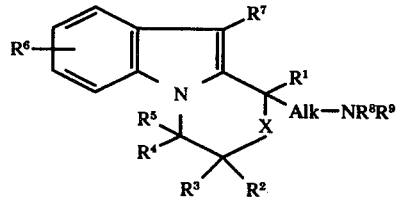

in which $R^1$ is lower alkyl or lower cycloalkyl; $R^2$, $R^3$, $R^4$ and $R^5$ are the same or different selected from the group consisting of hydrogen and lower alkyl; $R^6$ is hydrogen, lower alkyl, hydroxy; lower alkoxy, lower alkanoyloxy, nitro or halo, $R^7$ is lower alkyl; X is oxy; and Alk—$NR^8R^9$ is an amino(lower)alkyl radical in which Alk is an alkylene selected from the group consisting of $CR^{10}R^{11}$, $CR^{10}R^{11}CR^{12}R^{13}$, $CR^{10}R^{11}CR^{12}R^{13}CR^{14}R^{15}$ and $CR^{10}R^{11}CR^{12}R^{13}CR^{14}R^{15}CR^{16}R^{17}$ in which $R^{10}$, $R^{11}$, $R^{12}$, $R^{13}$, $R^{14}$, $R^{15}$, $R^{16}$ and $R^{17}$ are hydrogen or lower alkyl, and $R^8$ and $R^9$ are either the same or different selected from the group consisting of hydrogen and lower alkyl, or $R^8$ and $R^9$ together with the nitrogen atom to which they are joined form a heterocyclic amine radical selected from the group consisting of 1-pyrrolidinyl, piperidino, morpholino, piperazino, 4-(lower alkyl)-1-piperazinyl and 4-[hydroxy(lower)alkyl]-1-piperazinyl, or a corresponding pharmaceutically acceptable acid addition salt thereof.

23. The method of claim 22 in which the compound is 1,10-dimethyl-1-[(2-dimethylamino)ethyl]3,4-dihydro-1H-1,4-oxazino[4,3-a]indole.

24. The method of claim 22 in which the compound is 1,10-dimethyl-1-[2-(ethylamino)ethyl]-3,4-dihydro-1H-1,4-oxazino[4,3-a]indole.

25. The method of claim 22 in which the compound is 1,10-dimethyl-1-[3-(methylamino)propyl]-3,4-dihydro-1H-1,4-oxazino[4,3-a]indole.

26. The method of claim 22 in which the compound is 1,10-dimethyl-1-[3-(dimethylamino)propyl]-3,4-dihydro-1H-1,4-oxazino8 4,3-a]indole, as claimed in claim 1.

27. A pharmaceutical composition comprising a pharmaceutically acceptable carrier and about 0.1 to about 50 milligrams of a compound of formula

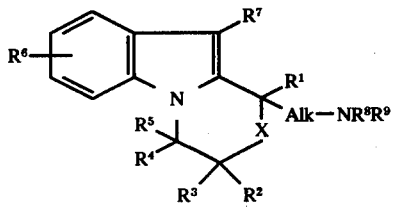

in which $R^1$ is lower alkyl or lower cycloalkyl; $R^2$, $R^3$, $R^4$ and $R^5$ are the same or different selected from the group consisting of hydrogen and lower alkyl; $R^6$ is hydrogen, lower alkyl, hydroxy, lower alkoxy, lower alkanoyloxy, nitro or halo; $R^7$ is lower alkyl; X is oxy; and Alk—$NR^8R^9$ is an amino(lower)alky radical in which Alk is an alkylene selected from the group consisting of $CR^{10}R^{11}$, $CR^{10}R^{11}CR^{12}R^{13}$, $CR^{10}R^{11}CR^{12}R^{13}CR^{14}R^{15}$ and $CR^{10}R^{11}CR^{12}R^{13}CR^{14}R^{15}CR^{16}R^{17}$ in which $R^{10}$, $R^{11}$, $R^{12}$, $R^{13}$, $R^{14}$, $R^{15}$, $R^{16}$ and $R^{17}$ are hydrogen or lower alkyl, and $R^8$ and $R^9$ are either the same or different selected from the group consisting of hydrogen and lower alkyl, or $R^8$ and $R^9$ together with the nitrogen atom to which they are joined form a heterocyclic amine radical selected from the group consisting of 1-pyrrolidinyl, piperidino, morpholino, piperazino, 4-(lower alkyl)-1-piperazinyl and 4-[hydroxy(lower)alkyl]-1-piperazinyl, or a corresponding pharmaceutically acceptable acid addition salt thereof.

28. The pharmaceutical composition of claim 27 in which the compound is 1,10-dimethyl-1-[(2-(dimethylamino)ethyl]-3,4-dihydro-1H-1,4-oxazino[4,3-a]indole.

29. The pharmaceutical composition of claim 27 in which the compound is 1,10-dimethyl-1-[2-(ethylamino)ethyl]-3,4-dihydro-1H-1,4-oxazino]4,3-a]indole hydrobromic acid addition salt.

30. The pharmaceutical composition of claim 27 in which the compound is 1,10-dimethyl-1-[3-(methylamino)propyl]-3,4-dihydro-1H-1,4-oxazino[4,3-a]indole hydrocholoric acid addition salt.

31. The pharmaceutical composition of claim 27 in which the compound is 1,10-dimethyl-1-[3-(dimethylamino)proply]-3,4-dihydro-1H-1,4-oxazino[4,3-a]indole hydrocholoric acid addition salt.

* * * * *